(12) United States Patent
Chu

(10) Patent No.: US 7,112,344 B2
(45) Date of Patent: Sep. 26, 2006

(54) **VAPOR FRACTION FROM SEEDS OF *GLYCINE MAX* (L.)MERR. AND COMPOSITION THEREOF**

(76) Inventor: I-Hung Chu, No. 216, Li-Lin E. Rd., Chio-Tou Country, Kaohsiung County (TW)

(*) Notice: Subject to any disclaimer, the term of this patent is extended or adjusted under 35 U.S.C. 154(b) by 233 days.

(21) Appl. No.: 10/638,889

(22) Filed: Aug. 11, 2003

(65) Prior Publication Data

US 2005/0037098 A1    Feb. 17, 2005

(51) Int. Cl.
*A61K 35/78* (2006.01)

(52) U.S. Cl. .................................................. 424/757
(58) Field of Classification Search ............... 424/757; 426/484, 430, 629
See application file for complete search history.

(56) References Cited

U.S. PATENT DOCUMENTS

| | | | | |
|---|---|---|---|---|
| 3,897,574 A * | 7/1975 | Pass | ............................ | 426/430 |
| 4,079,155 A * | 3/1978 | Kakade | ...................... | 426/634 |
| 4,452,743 A | 6/1984 | Günther | ....................... | 260/403 |
| 5,141,746 A * | 8/1992 | Fleury et al. | ............... | 424/757 |
| 6,248,910 B1 | 6/2001 | Franke | | |
| 2002/0009509 A1 | 1/2002 | Bombardelli | ............... | 424/757 |
| 2004/0151817 A1* | 8/2004 | Fukuda et al. | ............... | 426/549 |

FOREIGN PATENT DOCUMENTS

| | | |
|---|---|---|
| CN | 1073876 | 7/1993 |
| CN | 1188001 | 7/1998 |
| CN | 1397321 | 2/2003 |
| JP | 59021364 | 2/1984 |
| JP | 59 204120 | 11/1984 |
| JP | 1117767 | 5/1989 |
| JP | 01233207 | 9/1989 |
| JP | 4139132 | 5/1992 |
| JP | 6219926 | 8/1994 |
| JP | 08026937 | 1/1996 |
| JP | 9059166 | 3/1997 |
| JP | 09143087 | 6/1997 |
| JP | 10 158177 | 6/1998 |
| JP | 11206342 | 8/1999 |
| JP | 2000 080029 | 3/2000 |
| JP | 2000 169347 | 6/2000 |
| JP | 2000 316473 | 11/2000 |
| JP | 2001097842 | 4/2001 |
| JP | 2002-179529 | 6/2002 |
| JP | 2003 088320 | 3/2003 |
| KR | 2002027760 | 4/2002 |
| KR | 2003021811 | 3/2003 |
| SU | 845092 | 7/1981 |

OTHER PUBLICATIONS

English Translation of Title & Abstract of KR2002027760 Dated Apr. 15, 2002.
English Translation of Title & Abstract of KR2003021811 Dated Mar. 15, 2002.
An English Abstract of CN1073876 Dated Jul. 7, 1993.
An English Abstract of 2002-179529 Dated Jun. 26, 2002.
An English Abstract of CN1397321 Dated Feb. 19, 2003.
English language abstract of JP1117767. XP-002218979.
English language abstract of JP2001097842. XP-002218981.
English language abstract of JP4139132. XP-002218982.
English language abstact of JP9059166. XP-02218980.
English language abstract of SU845092. XP-002218978.
Chen, Yu-Jen et al. "The Effect of Tetrandrine and Extracts of *Centella asiatica* on Acute Radiation Dermatitis in Rats." *Biol. Pharm, Bull.* (1999), 22(7): 703-706.
Abe, Yoshinao and Muneyasu Urano. "Fraction Size-Dependent Acute Skin Reaction of Mice After Multiple Twice-A-Day Doses." *Int. J. Radiation Oncology Biol. Phys.* (1990), 18(2): 359-264.
King, W.W.K et al. "Evaluation of artificial skin (Integra) in a rodent model." *Burns*, (1997), 23(1): S30-S32.
Moulder, John E. And James J. Fischer. "Radiation Reaction of Rat Skin: The Role of the Number of Fractions and the Overall Treatment Time." *Cancer* (1976),37(6): 2762-2767.
Wang, Q. et al. "Electron irradiation slows down wound repair in rat skin: morphological investigation." *British Journal of Dermatology* (1994), 130: 551-560.
Wang, Hisan-Jenn et al. "Use of a Porcine Dermis Template to Enhance Widely Expanded Mesh Autologous Split-Thickness Skin Graft Growth: Preliminary Report." *J. Trauma*, (1997), 42(2): 177-182.
Hafemann, B. et al. "Use of a collagen/elastin-membrane for the tissue engineering of dermis" *Burns* (1999), 25: 373-384.
Gao, Z.-R. et al. "Porcine dermal collagen as a wound dressing for skin donor sites and deep partial skin thickness burns." *Burns* (1992), 18(6): 492-496.
Eloy, R. And A. M. Cornillac. "Wound healing of burns in rats treated with a new amino acid copolymer membrane" *Burns*, (1992), 18(5): 405-411.
Tabanca, Nurhayat et al. "Composition and Antimicrobiol Activity of the Essential Oils of *Micromeria cristata* subsp. *Phyrgia* and the Enantiomeric Distribution of Borneol." *J. Agric. Food. Chem.*, (2001), 49:4300-4303.
Hammerschmidt, F. J. et al. "Chemical Composition and Antimicrobial Activity of Essential Oils of *Jasonia candicans* and *J. montana*." *Planta Med.* (1993), 59: 68-70.
Oh, Kyu-Suk et al. "Inhibition of Nicotinic Receptor-Mediated Catacholamina Secretion by *Dryobalanops aromatica* in Bovine Adrenal Chromalfin Cells." *Pharmacological Research*, (2000), 42(6): 559-564.
Cyong, Jong-Chol et al. "Anti-*Bacteroides fragilis* Substance from Rhubarb." *J. Ethnopharmacology*, (1987), 19: 279-283.

(Continued)

*Primary Examiner*—Christopher R. Tate
(74) *Attorney, Agent, or Firm*—Ladas and Parry LLP

(57) ABSTRACT

The present invention mainly relates to a vapor fraction from seeds of *Glycine max* (L.) Merr. prepared by vaporizing a crude extract, and pharmaceutical composition thereof The present invention also provides the use of the vapor fraction in treating skin injuries, dermatological disorders, stimulating cell regeneration, and stimulating hair growth.

13 Claims, 34 Drawing Sheets
(34 of 34 Drawing Sheet(s) Filed in Color)

OTHER PUBLICATIONS

Matsuda, Hisashi et al. "Antioxidant Constituents from Rhubarb: Structural Requirements of Stilbenes for the Activity and Structures of Two New Anthraquinona Glucosides." *Bioorganic & Medicinal Chemistry*, (2001), 9: 41-50.

Hsiang, Chien-Yun et al. "Inhibitory Effect of Anti-pyretic and Anti-inflammatory Herbs on Herpes Simplex Virus Replication." *American J. Chinese Medicine*, (2001), 29 (3-4): 459-467.

Chunsheng, Li et al. "Protective Effect of Rhubarb in Endotoxin-Induced Acute Lung Injury." *J. Traditional Chinese Medicine* (2001), 21(1): 54-58.

Mori, Hiroshi et al. "Principle of the Bark of *Phellodendron amurense* to Suppress the Cellular Immune Response." *Planta Med.* (1994), 60: 445-449.

Takahata, Yasuhiro et al. "Highly Polymerized Procyanidins in Brown Soybean Seed Coat with a High Radical-Scavenging Activity." *J. Agric. Food Chem.* (2001), 49: 5843-5847.

Adlercreutz, Herman. "Phyto-oestrogens and cancer." *The Lancet Oncology*, (2002), 3: 364-373.

Matvienko, Oksana A. et al. "A single daily dose of soybean phytosterols in ground beef decreases serum total cholesterol and LDL cholesterol in young, mildly hypercholesterotemic men." *Am. J. Clin. Nutr.* (2002), 76: 57-64.

Maeda, Hiroshi et al. "High correlation between Lipid Peroxide Radical and Tumor-promoter Effect . . . " *Jpn. J. Cancer Res.* (1992), 83: 923-928.

Sugano, Michihiro and Kengo Akimoto. "Sesamin: A Multifunctional Gift from Nature." *Journal of the Chines Nutrition Society* (1993), 18: 1-11.

Jiao, Ying et al. "Furanofuran Lignan Metabolism as a Function of Seed Maturation in *Sesamun indicum*: Methylenedioxy Bridge Formation." *Phytochemistry* (1998), 49(2): 387-394.

Fukuda, Yasuko et al. "Studies on Antioxidative Substances in Sesame Seed." *Agric. Biol. Chem.* (1985), 49(2): 301-306.

Minamiyama, Yukiko et al. "Antioxidative Effects of a Processed Grain Food." *J. Nutr. Sci. Vitaminol.*, (1994), 40: 467-447.

Wu, S.-J. et al. "Evaluation of hepatoprotective activity of Legumes." *Phytomedicine* (2001), 8(3): 213-219.

English abstract of JP 59021364, dated Feb. 3, 1984.

English abstract of JP 6219926, dated Aug. 9, 1994.

English abstract of JP 2003 0088320, dated Mar. 25, 2003.

English abstract of JP 2000 169347, dated Jun. 20, 2000.

English abstract of JP 2000 316473, dated Nov. 21, 2000.

English abstract of JP 09143087, dated Jun. 3, 1997.

Engllish abstract of JP 111206342, dated Aug. 3, 1999.

English abstract of CN 1188001, dated Jul. 22, 1998.

English abstract of JP 2000 080029, dated Mar. 21, 2000.

English abstract of CN 1397321, dated Feb. 19, 2003.

English abstract of JP 10 158177, dated Jun. 16, 1998.

English abstract of JP 59 204120, dated Nov. 19, 1984.

English abstract of JP 01233207, dated Sep. 19, 1989.

English abstract of JP 08026937, dated Jan. 30, 1996.

* cited by examiner

VAPOR FRACTION FROM SEEDS OF GLYCINE MAX (L.)MERR. AND COMPOSITION THEREOF

BACKGROUND OF THE INVENTION

1. Field of the Invention

The invention mainly relates to a vapor fraction from the seeds of *Glycine max* (L.) Merr. which has effects in treating skin injuries, in treating dermatological disorders, in stimulating cell regeneration, and in stimulating hair growth.

2. Description of the Related Art

*Glycine max* (L.) Merr., including soybean and black soybean, is one of the most important sources of oil and proteins in the world. For instance, soybeans can be processed to obtain an edible, semi-drying oil that is used as salad oil, or for manufacture of margarine and shortening. Soybean oil can be also used in the manufacture of paints, linoleum, oilcloth, printing inks, soaps, insecticides, and disinfectants. Besides, lecithin phospholipids obtained from the by-products of the oil industry, can be used as wetting and stabilizing agents in food, cosmetics, pharmaceuticals, leathers, paints, plastics, soaps, and detergents. Soy meal is a very protein-rich feeding stuff for livestock. In addition, soybean protein can be used in manufacture of synthetic fibers, adhesives, textile sizing, waterproofing, fire-fighting foams and so on.

In medical use, soybeans have been reported to have effects on many diseases.

Soybean can be used as a nutritious supplement for regulating the functions of bowels, heart, kidney, liver, and stomach. Since soybean oil contains a high amount of unsaturated fatty acids, it can be used to combat hypercholesteremia. Medical lecithin from soybeans functions as a lipotropic agent. In addition, tigmasterol known as an anti-stiffness factor, and sitosterol used as a replacement for diosgenin in some antihypertensive drugs, were prepared from soybeans. Isoflavones and phyto-oesterogens found in soybeans have been suggested to have a preventive effect against various cancers comprising breast, prostate, and colon cancers (Adlercreutz, H.; Phyto-oestrogens and cancer. *The Lancet Oncology,* 2002, Vol. 3, p. 364–373). Consumption of phytosterol-supplemented margarine was also found to lower total plasma cholesterol and LDL-cholesterol concentrations in older middle-aged hypercholesterolemic individuals (Matvienko, O. A., Lewis, D. S., Swanson, M., Aendt, B., Rainwater, D. L., Stewart, J., and Alekel, D. L.; A single daily dose of soybean phytosterols in ground beef decreases serum total cholesterol and LDL cholesterol in young, mildly hypercholesterolemic men. *Am J Clin Nutr.,* 2002, 76, p. 57–64).

Some extracts from soybean have been also reported to have pharmaceutical effects. 1,1-diphenyl-2-picrylhydrazyl (DPPH) radical-scavenging activity of the 70% aqueous acetone extract from the seed coat of the brown soybean variety, Akita-Zairai, was disclosed (Takahata. Y., O.-Kameyama, M., Furuta, S., Takahashi, M., and Suda, I.; Highly polymerized procyanidins in brown soybean seed coat with a high radical-scavenging activity. *J. Agric. Food Chem.,* 2001, 49, p. 5843–5847). An extract from germ extracts, soybean, rice bran, tear grass, sesame, wheat, citron, green tea, green leaf extract, and malted rice, which were slowly roasted under a powdered oure at less than 60° C. and fermented with *Aspergillus oryzae* over 3 days to transform each ingredient into low molecular weight substances, was found to have antioxidative effects (Minamiyama, Y., Yoshikawa, T., Tanigawa, T., Takahashi, S., Naito, Y., Ichikawa, H., and Kondo, M.; Antioxidative effects of a processed grain food. *J. Nutr. Sci. Vitaminol.,* 1994, 40, p. 467–477). Boiled extracts of green leaves of carrot, crucifers, and beans comprising black bean, red bean, mung bean, and soybean showed to have great anti-tumor-promoter and radical-scavenging activities (Maeda. H., Katsuki, T., Akaike, T. and Yasutake. R.; High correlation between lipid peroxide radical and tumor-promoter effect: suppression of tumor promotion in the Epstein-Barr virus/B-lymphocyte system and scavenging of alkyl peroxide radicals by various vegetable extracts. *Jpn. J. Cancer Res.,* 1992, 83, p. 923–928). Water extract of black bean also reported to effect on acetaminophen-induced liver injury by measuring serum glutamate-oxalate-transaminase (sGOT) and serum glutamate-pyruvate-transaminase (sGPT) activities in rats (Wu, S.-J., Wang, J.-S. and Chang, C.-H.; Evaluation of hepatoprotective activity of legumes. *Phytomedicine,* 2001, Vol. 8(3), p. 213–219). An extract of soybean seed with an extracting liquid consisting of mixed system of low aliphatic alcohol and low boiling ester was shown as a refresh drink agent for quenching thirst (JP Patent No. 1117767).

Some specific extracts from soybean had been found to be applied in cosmetics or pharmaceuticals in treating some skin disease.

Soya extract, which contains sphingomyelins and phospholipids in defined ratios was disclosed to be used in cosmetics for the treatment of dry skin (U.S. Patent Pub. No. US2002/0009509 A1). Such extract was produced by extracting ripe whole soya beans or oil-free soya flour using aliphatic alcohols alone or in a mixture with water and followed by the treatment with aliphatic hydrocarbons and with aliphatic ketones. Therefore, the extract is liposoluble.

An acne medicine, comedon production inhibitor or cosmetic composition containing one or more plant extracts selected from whey, and a *Phellodendeon amurense* Ruprecht extract, and further one or more extracts selected from *Scutellaria baicalensis* Geoegi, *Symphytum officinale* Linne, and *Glycine max* (L.) Merrill, was found to be effective for preventing or treating skin diseases such as the acne or inflammatory chapped skin caused by the acne (JP Patent No. 2001097842). The composition can be used for production of general drinks, foods, and so on.

Malonylisoflavone glycoside obtained from soybean or an extracted solution of soybeans with water and, for example, malonyldaizin etc. was as an epithelial cell proliferation promoter (JP Patent No. 9059166). The glycoside is obtained by immersing peeled soybeans in water adjusted to pH 7.5 to pH 9.0 with caustic soda at 45–65° C. for 2–4 hours, removing the soybeans to give the immersion water as an extracted solution with water, removing protein from the extracted solution by an ultrafilter membrane to give a filtrate, bringing the filtrate into contact with an adsorbent and eluting the glycoside from the adsorbed material by using an aqueous solution of an alcohol or an alkali aqueous solution of an alcohol.

Products of fermenting soybean by microorganisms were also applied as anti-active oxygen action compositions, agents, foods, cosmetics and medicines (such as JP Patent No. 4139132).

However, none of the prior art teaches or suggests that a low concentration or free of alcohol vapor fraction from *Glycine max* (L.) Merr. which is prepared easily in treating skin injuries and dermatological disorders.

SUMMARY OF THE INVENTION

The present invention provides a vapor fraction from the seeds of *Glycine max* (L.) Merr., which shows dramatic effects of treating skin injuries, treating dermatological disorders, stimulating cell regeneration, and stimulating hair growth.

The vapor fraction of the invention is prepared by the process comprising the steps of:

(a) providing a crude extract of the seeds in an alcohol solution containing alcohol at the concentration lower than about 15% wt. or in water; and (b) vaporizing the crude extract at a barometric pressure lower than about 1 atm and at a temperature lower than about 110° C. to obtain the vapor fraction.

The vapor fraction is different from any known seed extracts of *Glycine max* (L.) Merr. because its fingerprint shows a unique profile through a high performance liquid chromatography (HPLC). In particular, the HPLC spectrogram of the 50 μL of vapor fraction taken at 200 nm using Waters Sphersorb™-ODS2 column with an inner diameter (I.D.) of 4.6 mm, a length (L) of 250 nm and a particle size of 5 μm comprises peaks at retention time of 2.910, 5.190, 13.190, and 50.815 minutes with the coefficient of variation of 8%, where mobile phase at 0 to 5 minutes is 95% $H_2O$/5% $CH_3CN$; at 5 to 30 minutes is 95% $H_2O$/5% $CH_3CN$ in gradient, at 30 to 80 minutes is 75% $H_2O$/25% $CH_3CN$ in gradient; at 80 to 100 minutes is 0% $H_2O$/100% $CH_3CN$ in gradient; at 100 to 101 minutes is 0% $H_2O$/100% $CH_3CN$ in gradient; and at 101 minute is 95% $H_2O$/5% $CH_3CN$; and a flow rate is 1 mL/min.

The invention also provides a composition comprising the vapor fraction of the invention. In particular, the composition can be used for a pharmaceutical composition, a cosmetic composition or a skin cleaning composition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates the HPLC spectrogram of Fraction 1 obtained by the process according to the invention.

FIG. 2 illustrates the HPLC spectrogram of Fraction 3 obtained by the process according to the invention.

FIG. 4 illustrates the picture of hair growth on full thickness skin wounds treated with the ointment according to the invention in Example 3.

DETAILED DESCRIPTION OF THE INVENTION

Figure 1A:
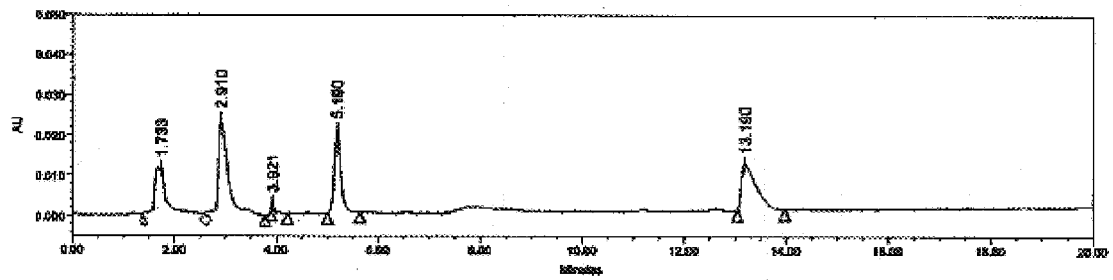
FIG. 1a: 0 to 20 minutes.

According to the invention, the vapor fraction of *Glycine max* (L.) Merr. is unexpectedly found to have dramatic effects in treating skin injuries, treating dermatological disorders, stimulating cell regeneration, and stimulating hair growth.

According to the present invention, a vapor faction from seeds of *Glycine max* (L.) Merr. is prepared by the process comprising the steps of:

(a) providing a crude extract of the seeds in an alcohol solution containing alcohol at the concentration lower than about 15% wt. or in water; and (b) vaporizing the crude extract at a barometric pressure lower than about 1 atm and at a temperature lower than about 110° C. to obtain the vapor fraction.

It is unexpectedly found that a vapor fraction obtained from a crude extract of the seeds in an alcohol solution containing alcohol at the concentration lower than about 15% wt. or in water has effect in dermatology. The vapor fractions are easily prepared. Medicinal or cosmetic products prepared from seeds of *Glycine max* (L.) Merr. are advantageous because (1) soybeans have been consumed for a long time and are believed to be non-toxic; and (2) soybeans are not expensive.

In an embodiment of the invention, the crude extract from the seeds of *Glycine max* (L.) Merr. is obtained by an extraction with an alcohol solution at a concentration lower than about 15% wt, or with water. Any methods for obtaining crude extracts from plant seeds commonly used in the art can be used to practice the invention. For instance, the crude extract can be obtained by dividing the seeds into small pieces in any conventional manners such as grinding, stirring, disturbing, cutting or mincing, and immersing them in an alcohol solution at a concentration lower than about 15% wt. In a preferred embodiment, the concentration of alcohol is lower than about 10% wt, more preferably about 3% wt or about 2% wt. According to the invention, the crude extract can also be extracted with water. In a preferred embodiment, the pieces of seeds are immersed in alcohol or water ranging from about 5 parts to about 10 parts by weight. Any ways of dividing the seeds and extracting the divided seeds commonly used in the art can be used to practice the present invention.

According to the invention, crude extract is vaporized at a barometric pressure lower than about 1 atm and at a temperature lower than about 110° C., preferably from about 60° C. to about 110° C. The vapor fraction can be collected in a liquid form by chilling the vapor.

In a preferred embodiment of the invention, a process of vaporizing the crude extract at a given barometric pressure and temperature, and collecting said vapor fraction by chilling the vapor can be performed in a rotary evaporator where the vapor is evaporated to the condensing tube supplied with cold water, and then the vapor is chilled by passing through the condensing tube to collect the vapor fraction in a liquid form. The manipulation is simple and the cost is low.

The vapor fraction according to the invention can be analyzed and identified with a high performance liquid chromatography (HPLC). For instance, the HPLC spectrogram of the 50 μL of vapor fraction taken at 200 nm using Waters Sphersorb™-ODS2 column with an inner diameter (I.D.) of 4.6 mm, a length (L) of 250 mm and a particle size of 5 μm comprises peaks at retention time of 2.910, 5.190, 13.190, and 50.815 minutes with the coefficient of variation of 8%, where mobile phase at 0 to 5 minutes is 95% $H_2O$/5% $CH_3CN$; at 5 to 30 minutes is 95% $H_2O$/5% $CH_3CN$ in gradient, at 30 to 80 minutes is 75% $H_2O$/25% $CH_3CN$ in gradient; at 80 to 100 minutes is 0% $H_2O$/100% $CH_3CN$ in gradient; at 100 to 101 minutes is 0% $H_2O$/100% $CH_3CN$ in gradient; and at 101 minute is 95% $H_2O$/5% $CH_3CN$; and a flow rate is 1 mL/min. According to the spectrogram, substances in the vapor fraction show strong polarity. They are much different from other ingredients disclosed in the prior art. For example, daidzein and genistein have four rings in their structures, and have weak polarity.

In one preferred embodiment of the invention, several herbals are added for assisting seeds of *Glycine max* (L.) Merr. in treating skin injuries, treating dermatological disorders, stimulating cell regeneration, and stimulating hair growth. According to the invention, a vapor fraction is obtained from raw materials comprising seeds of *Glycine max* (L.) Merr. and at least one material selected from the group consisting of seeds of *Sesamum indicum*, seeds of *Phaseolus radiatus* L. and antimicrobial herbals. The preparation of vapor fraction from the raw material and the analysis and identification of the vapor fraction are described above. Preferably, the antimicrobial herbal is selected from the group consisting of dry rhizomes *Rheum palmatum* L., dry rhizomes of Rhei Rhizoma, dry barks of *Phellodendron amurense* Rupr., and dry barks of Phellodendri Cortex. In another aspect, the raw materials preferably comprise about 40 to about 100% of seeds of *Glycine max* (L.) Merr., 0 to about 50% of seeds of *Sesamum indicum*, 0 to about 50% of seeds of *Phaseolus radiatus* L. and 0 to about 30% of antimicrobial herbal.

In one more preferred embodiment of the invention, the raw materials comprise about 70% of seeds of *Glycine max* (L.) Merr., about 20% of seeds of *Sesamum indicum*, about 5% of dry rhizomes of *Rheum palmatum* L. or dry rhizomes of Rhei Rhizoma, and about 5% of dry barks of *Phellodendron amurense* Rupr. or dry barks of Phellodendri Cortex. The raw material is in about 2% of alcohol.

In another more preferred embodiment of the invention, the raw materials comprise about 80% of seeds of *Glycine max* (L.) Merr. and about 20% of seeds of *Phaseolus radiatus* L. The raw material is in about 2% of alcohol.

In still another more preferred embodiment of the invention, the raw materials comprise about 80% of seeds of *Glycine max* (L.) Merr. and about 20% of seeds of *Sesamum indicum*. The raw material is in about 2% of alcohol.

In still another more preferred embodiment of the invention, the raw materials comprise about 90% of seeds of *Glycine max* (L.) Merr. and about 10% of dry rhizomes of *Rheum palmatum* L. or dry rhizomes of Rhei Rhizoma. The raw material is in water.

In still another more preferred embodiment of the invention, the raw materials comprise about 80% of seeds of *Glycine max* (L.) Merr., about 10% of seeds of *Sesamum indicum* and about 10% of dry rhizomes of *Rheum palmatum* L. or dry rhizomes of Rhei Rhizoma. The raw material is in water.

In the most preferred embodiment of the invention, the raw materials comprise about 53% of seeds of *Glycine max*

(L.) Merr., about 20% of seeds of *Sesamum indicum*, about 17% of seeds of *Phaseolus radiatus* L., about 5% of dry rhizomes of *Rheum palmatum* L. or dry rhizomes of Rhei Rhizoma, and about 5% of dry barks of *Phellodendron amurense* Rupr. or dry barks of Phellodendri Cortex. The raw material is in about 3% or in about 2% of alcohol or in water. Furthermore, the HPLC spectrogram of the 50 μL of vapor fraction taken at 200 nm using Waters Sphersorb™-ODS2 column with an inner diameter (I.D.) of 4.6 mm, a length (L) of 250 mm and a particle size of 5 μm comprises peaks at retention time of 2.896, 5.111, 12.944, and 46.603 minutes with the coefficient of variation of 8%, where mobile phase at 0 to 5 minutes is 95% $H_2O$/5% $CH_3CN$; at 5 to 30 minutes is 95% $H_2O$/5% $CH_3CN$ in gradient, at 30 to 80 minutes is 75% $H_2O$/25% $CH_3CN$ in gradient; at 80 to 100 minutes is 0% $H_2O$/100% $CH_3CN$ in gradient; at 100 to 101 minutes is 0% $H_2O$/100% $CH_3CN$ in gradient; and at 101 minute is 95% $H_2O$/5% $CH_3CN$; and a flow rate is 1 mL/min.

The invention also provides a composition comprising the vapor fraction according to the invention. Preferably, the composition is selected from the group consisting of a pharmaceutical composition, a cosmetic composition and a skin cleaning composition. In a preferred embodiment according to the invention, the composition further comprises an antimicrobial agent such as borneol. Preferably, the amount of the vapor fraction according to the invention ranges from about 70% to about 80% of total composition weight.

In one embodiment of the invention, the composition further comprises borneol, stearic acid, stearyl alcohol, palmitic acid, cetyl alcohol, beewax and polyoxy ethylene sorbitan monostearate (POE) to form an ointment for easily applied on a subject.

A method for treating skin injuries or dermatological disorders comprising applying the composition according to the invention at a sufficient amount effective for treating skin injuries, treating dermatological disorders, stimulating cell regeneration, and stimulating hair growth.

The vapor fraction according to the invention is useful for treating skin injuries, treating dermatological disorders, stimulating cell regeneration, and stimulating hair growth. For example, the skin injuries or dermatological disorders contains burn injury, sunburns, irradiation injury, acute and chronic trauma, ecchymosis, dermatitis, macule, papule, nodule, vesicle, bulla, pustule, wheal, plaque, cyst, scales, crust, fissure, ulcer, acne, xeroderma, desquamation, itch, allergic dermatitis, exanthema, and hair follicle defect. Preferably, the composition according to the invention is effective in treating burn injury, irradiation injury, acute and chronic trauma, dermatitis, gangrene, chronic stasis ulcer, abrasion, atopic dermatitis, suture wounds, diabetes mellitus wounds, and hair follicle defect.

In the animal model described below, the vapor fraction according to the invention has been proved to be effective for curing large area skin deficient without granulation, epulosis and allergy. In addition, hair follicle defect could be cured and hairs could grow again without erythema or eschar. The healing rates and conditions of the wounds treated with the vapor fraction according to the present invention are much better than those with conventional drugs. The wounds treated with the vapor fraction according to the present invention were healed without scar, and the skin color of the healed wound was the same as normal skin color. Besides, in the histological examination, the skin tissues of the wounds treated with the vapor fraction according to the present invention did not show fibrous degeneration that usually caused enormous damage on appearance and produced complex reconstructive surgenes.

In addition, no allergic reaction, inflammation, blain, or rash were found in the wounds treated with the vapor fraction of the invention. After the treatment, the accessory organs and cells of the wound grew as the same as those of normal skins. By contrary, the wounds treated with a conventional drug have less numbers of accessory organs and cells, and the fiber width of the wounds was larger than the normal.

Furthermore, the vapor fraction according to the invention is effective in treating irradiation injuries. So far, no drugs are effective in treatment of irradiation injuries. It is unexpectedly found that in a subject suffering from irradiation injuries, the wounds after the treatment with the vapor fraction show little damage in hairs and no allergy.

In addition, neither inflammation nor tissue contraction, which are usually observed in wound healing, is found in the wounds healed with the vapor fraction according to the invention. The vapor fraction is effective in healing the wounds in which the dermal is damaged. Therefore, the invention provides a better, convenient, and economical way for treating large area and dermatological wounds.

The following Examples are given for the purpose of illustration only and are not intended to limit the scope of the present invention.

EXAMPLE 1

Preparation of Vapor Fraction from Seeds of *Glycine max* (L.) Merr.

Raw materials comprising seeds of *Glycine max* (L.) Merr., seeds of *Sesamum indicum*, seeds of *Phaseolus radiatus* L., dry rhizomes of *Rheum palmatum* L. or dry rhizomes of Rhei Rhizoma, and dry barks of *Phellodendron amurense* Rupr. or dry barks of Phellodendri Cortex were ground and extracted with 8 parts by weight of alcohol or distilled water to obtain a crude extract. The contents were shown in Table 1. The vapor fraction was obtained by vaporizing the crude extract in a rotary evaporator (EYELA N-1000S, 1000S-W) at a pressure of lower than 1 atm and a temperature of 60° C., and passing through a condensing tube supplied with cold water.

TABLE 1

| Raw materials | Fraction No: | | | | | | | |
|---|---|---|---|---|---|---|---|---|
| | 1 | 2 | 3 | 4 | 5 | 6 | 7 | 8 |
| Seeds of *Glycine max* (L.) Merr. (%) | 100 | 70 | 53 | 80 | 0 | 80 | 90 | 80 |
| Seeds of *Sesamum indicum* (%) | 0 | 20 | 20 | 0 | 0 | 20 | 0 | 10 |
| Seeds of *Phaseolus radiatus* L. (%) | 0 | 0 | 17 | 20 | 0 | 0 | 0 | 0 |
| dry rhizomes of *Rheum palmatum* L. or dry rhizomes of Rhei Rhizoma (%) | 0 | 5 | 5 | 0 | 0 | 0 | 10 | 10 |
| dry barks of *Phellodendron amurense* Rupr. or dry barks of Phellodendri Cortex (%) | 0 | 5 | 5 | 0 | 0 | 0 | 0 | 0 |
| Solution | | | | | | | | |
| Distilled water (%) | 98 | 98 | 98 | 98 | 100 | 98 | 100 | 100 |
| Ethanol (%) | 2 | 2 | 2 | 2 | 0 | 2 | 0 | 0 |

Figure 1B:
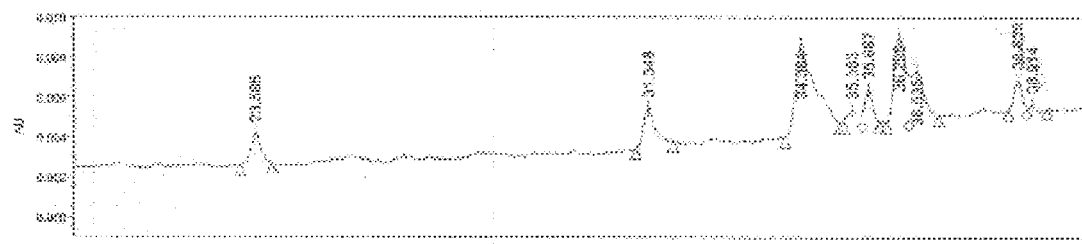
FIG. 1b: 20 to 40 minutes.
Figure 1C:
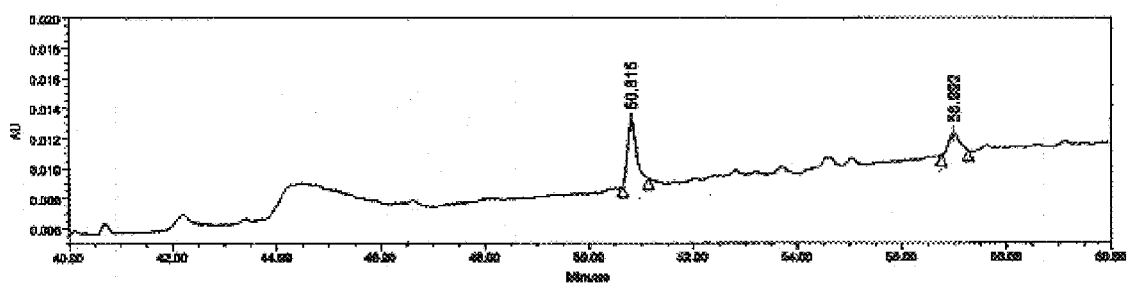
FIG. 1c: 40 to 60 minutes.

The result of the HPLC for 50 μL of Fraction 1 was shown in FIG. 1. The HPLC was preformed through Waters Sphersorb™-ODS2 column with an inner diameter (I.D.) of 4.6 mm, a length (L) of 250 mm and a particle size of 5 μm where the mobile phase at 0 to 5 minutes was 95% $H_2O$/5% $CH_3CN$; at 5 to 30 minutes was 95% $H_2O$/5% $CH_3CN$ in gradient, at 30 to 80 minutes was 75% $H_2O$/25% $CH_3CN$ in gradient; at 80 to 100 minutes was 0% $H_2O$/100% $CH_3CN$ in gradient; at 100 to 101 minutes was 0% $H_2O$/100% $CH_3CN$ in gradient; and at 101 minute was 95% $H_2O$/5% $CH_3CN$ and the flow rate was 1 mL/min. The HPLC was conducted with Waters Alliance 2795 HT, and the spectrogram was taken from 190 to 400 nm by Waters Photo Diode Array 2996. As shown in the spectrogram taken at 200 nm, there were sharp peaks at the retention time of 2.910, 5.190, 13.190, and 50.815 minutes with the coefficient of variation of 8%.

Figure 2A:
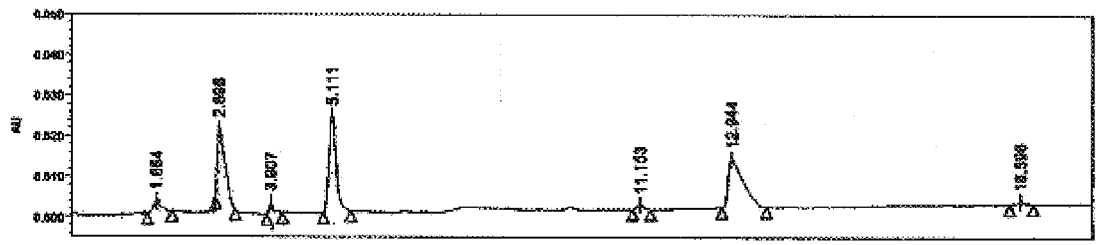
FIG. 2a: 0 to 20 minutes.
Figure 2B:
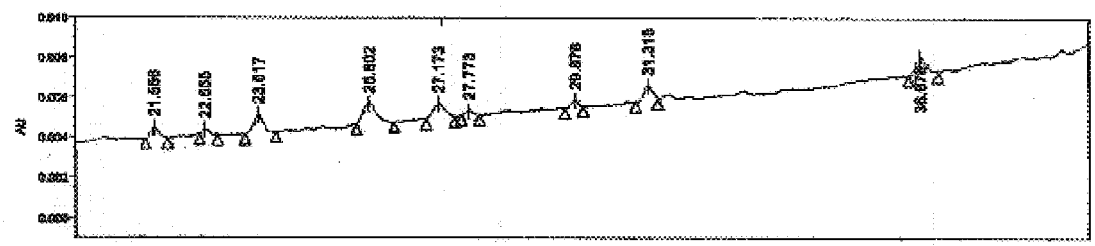
FIG. 2b: 20 to 40 minutes.
Figure 2C:
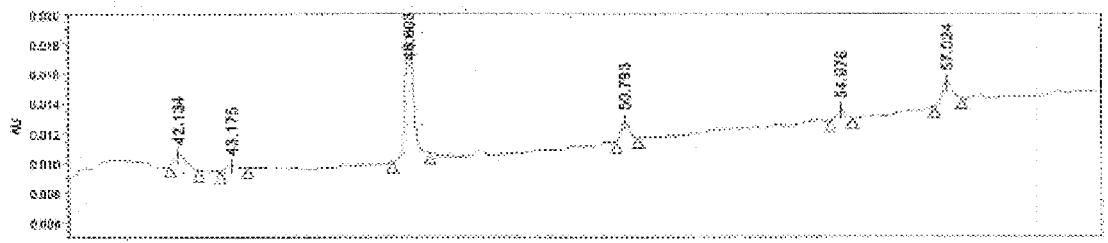
FIG. 2c: 40 to 60 minutes.

The result of the HPLC for 50 μL of Fraction 3 was shown in FIG. 2. The HPLC was preformed through Waters Sphersorb™-ODS2 column with an inner diameter (I.D.) of 4.6 mm, a length (L) of 250 mm and a particle size of 5 μm where the mobile phase at 0 to 5 minutes was 95% $H_2O$/5% $CH_3CN$; at 5 to 30 minutes was 95% $H_2O$/5% $CH_3CN$ in gradient, at 30 to 80 minutes was 75% $H_2O$/25% $CH_3CN$ in gradient; at 80 to 100 minutes was 0% $H_2O$/100% $CH_3CN$ in gradient; at 100 to 101 minutes was 0% $H_2O$/100% $CH_3CN$ in gradient; and at 101 minute was 95% $H_2O$/5% $CH_3CN$ and the flow rate was 1 mL/min. The HPLC was conducted with Waters Alliance 2795 HT, and the spectrogram was taken from 190 to 400 nm by Waters Photo Diode Array 2996. As shown in the spectrogram taken at 200 nm, there were sharp peaks at the retention time of 2.896, 5.111, 12.944, and 46.603 minutes with the coefficient of variation of 8%.

EXAMPLE 2

Preparation of Ointment

The ointments according to the invention were exemplified in Table 2:

TABLE 2

|  | Content (wt) |
| --- | --- |
| Fraction | 77% |
| Borneol | 0.6% |
| Stearic acid | 5% |
| Stearyl alcohol | 4% |
| Palmitic acid | 4% |
| Cetyl alcohol | 5% |
| Beewax | 2% |
| Polyoxy ethylene sorbitan monostearate | 2.4% |

The ointments of the invention can be prepared in any conventional methods commonly used in this art.

EXAMPLE 3

Effects on Full Thickness Skin Wounds in Rabbits

Treatment of Animals:

Five female adult New Zealand White rabbits weighting 2.9 to 3.1 Kg was taken as an animal model. Each rabbit was caged alone and feed with chow and water. The rabbits were anaesthetized with 25 to 40 mg/Kg of ketamine HCl. The back of each rabbit was thoroughly clipped and six areas of the full thickness skin (wherein each area is of 1.5×1.5 $cm^2$) were excised, wherein the full thickness skin comprised epidermis, dermis, and panniculus carnosus.

Dosage and Frequency:

The six areas of the wound of each rabbits were treated twice a day with the ointments comprising Fractions 1 to 6, respectively. The ointments were topically applied on the wounds at an amount of 0.35 g per $cm^2$.

Clinical Wound Evaluation:

The wounds were observed everyday and photographed with a referential scale three times a week under a uniform condition of light, a focal length, and aperture to record the process of the wound healing. Besides, the sizes of the wounds were also measured and given in Table 3.

TABLE 3

| | Wound area treated with the ointment comprising Fraction No. (%) | | | | | |
| --- | --- | --- | --- | --- | --- | --- |
| Day | 1 | 2 | 3 | 4 | 5 | 6 |
| 0 | 100.0 | 100.0 | 100.0 | 100.0 | 100.0 | 100.0 |
| 2 | 105.5 | 103.1 | 103.8 | 105.1 | 120.9 | 117.3 |
| 5 | 108.9 | 110.2 | 105.5 | 100.4 | 134.4 | 130.0 |
| 8 | 80.0 | 72.9 | 78.3 | 75.3 | 93.0 | 96.0 |
| 11 | 49.4 | 47.1 | 49.4 | 39.2 | 54.0 | 55.1 |
| 14 | 17.9 | 15.1 | 17.0 | 16.5 | 21.0 | 20.4 |
| 17 | 7.7 | 6.2 | 9.4 | 9.1 | 10.2 | 10.7 |
| 19 | 3.6 | 4.1 | 4.1 | 4.4 | 7.4 | 5.0 |
| 22 | 0.5 | 0.5 | 0.0 | 0.5 | 1.7 | 0.5 |
| 25 | 0.0 | 0.0 | 0.0 | 0.0 | 0.0 | 0.0 |

Figure 3:
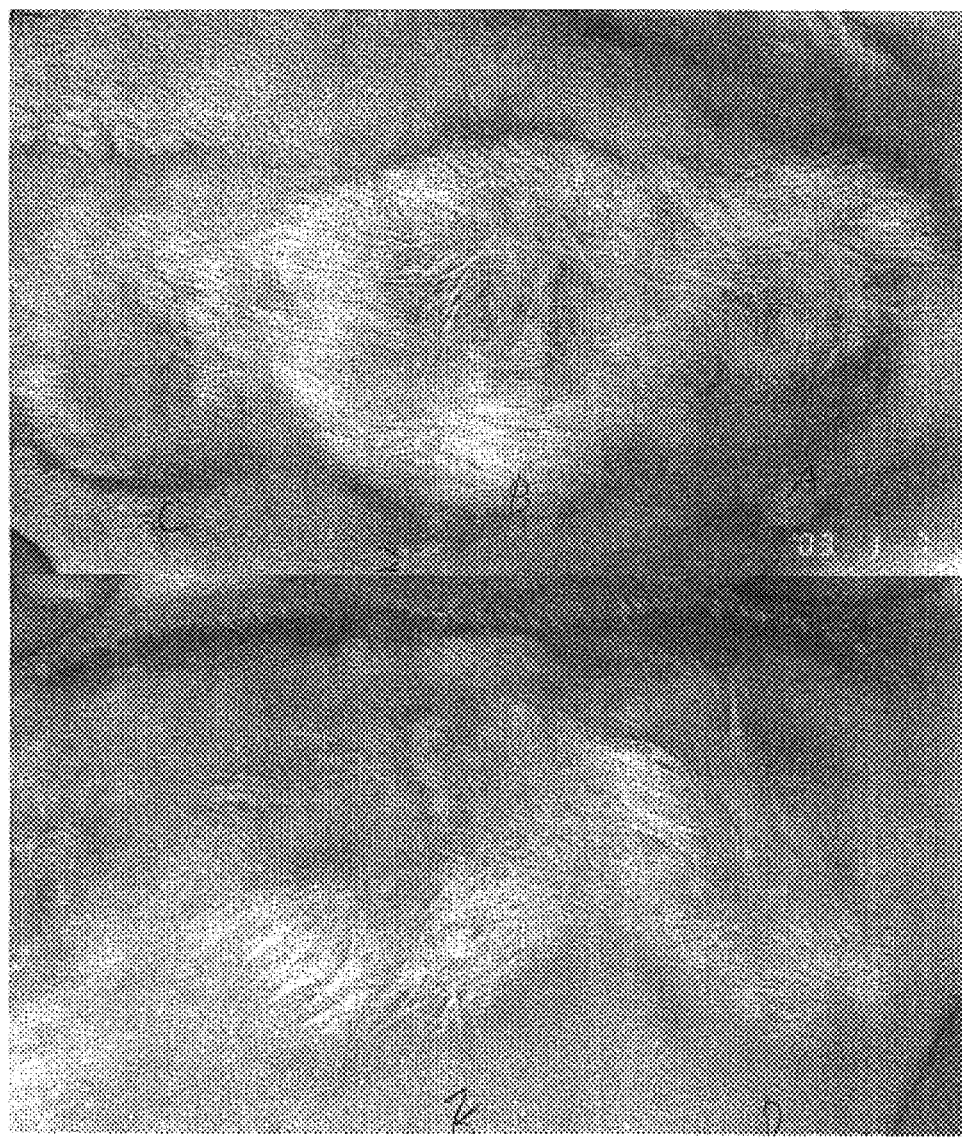
FIG. 3 illustrates the picture of full thickness skin wounds treated with the ointment according to the invention in Example 3.

The result show that the wounds were all healed (as shown in FIG. 3). The excipient according to the invention (ointment comprising Fraction 5) also had an effect in treating full thickness skin wounds.

Figure 4A:
FIG. 4a: the ointments comprising Fractions 1 to 3.
Figure 4B:
FIG. 4b: the ointments comprising Fractions 4 to 6.

Hair Growth Evaluation:

The length of new hair was measured. Hairs of the all wounds treated with the ointments comprising Fractions 1 to 6 were of about 1.76 cm long in average (as shown in FIG. 4), and those of the areas without treatment were average 0.1 to 0.2 cm.

The result showed that the vapor fraction according to the invention had an ability to repair hair follicle defect and stimulated hair growth. Besides, the excipient according to the invention was effective to enhance hair growth, too.

EXAMPLE 4

Effects on Full Thickness Skin Wounds in Rats

Treatment of Animals:

The male adult Sprague-Dawley rats were purchased from Laboratory Animal Center of the National Cheng Kung University in Taiwan. The rats weighting 300 to 350 g were anaesthetized with 25 to 40 mg/Kg of ketamine HCl. The back of each rat was thoroughly clipped using an electrical clipper. Each rat was caged alone and feed with chow and water. For each rat, the full thickness skin of an area of 2.5×2.5 $cm^2$ was excised, wherein the full thickness skin comprises epidermis, dermis, and panniculus camosus (B. Hafemann et al. Use of a collagen/elastin-membrane for the tissue engineering of dermis. *Burns*. 1999;25:373–384; H.-J. Wang et al. Use of a Porcine Dermis Template to Enhance Widely Expanded Mesh Autologus Split-Thickness Skin Graft Growth. *J Trauma*. 1997 February;42(2):177–182).

Dosage and Frequency:

Two-experiment group of rats were treated with the ointments comprising Fractions 7 and 8 as given in Example 2 and each group contained three rats. The pharmaceutical compositions were topically applied on the wounds at an amount of 0.35 g per cm$^2$ and 0.1 to 0.2 cm height. All the wounds were dressed by sterile gauze and elastic bandage, and the dressing was changed everyday.

The evaluation methods analogous to those in Example 3 were used and the sizes of the wounds were measured and given in Table 4.

TABLE 4

| | Wound area treated with the ointment comprising Fraction No. (%) | |
|---|---|---|
| Day | 7 | 8 |
| 0 | 100 | 100 |
| 2 | 85.3 | 102.5 |
| 5 | 64.3 | 71.4 |
| 9 | 24 | 34.5 |
| 12 | 18.6 | 25.2 |
| 15 | 9.3 | 13.4 |
| 17 | 3.1 | 8.4 |
| 20 | 0.4 | 2.5 |
| 23 | 0.0 | 0.0 |

The wounds treated with the ointments comprising Fractions 7 and 8 were healed. Particularly, the wound area treated with the pharmaceutical composition comprising Fraction 7 decreased more quickly.

EXAMPLE 5

Effects on Healing of Deep Partial Skin Thickness Burn

Treatment of Animals:

The female adult Sprague-Dawley rats were purchased from Laboratory Animal Center of the National Cheng Kung University in Taiwan. Nine rats weighting 230 to 280 g were anaesthetized with 25 to 40 mg/Kg of ketamine HCl. The back of each rat was thoroughly clipped using an electrical clipper at a predicted wound area in the middle of the back. Each rat was caged alone and feed with chow and water. Burn wounds of the rats were produced by using the method as described by Walker and Mason (Z-R. Gao et al. Porcine dermal collagen as a wound dressing for skin donor sites and deep partial skin thickness burns. Burns. 1992;18(6):492–496), in which the dorsal skin surface was exposed to water at 75° C. for 15 seconds through a template designed to produce a deep partial skin thickness burn with the area of 4×4 cm$^2$.

Dosage and Frequency:

The experiment group (G3) of rats was treated with Pharmaceutical composition according to the invention that comprises Fraction 9 similar to Fraction 3 except the content of alcohol being 3% as given in Example 2. There were one control group (G1) of rats without treatment and one comparative group (G2) of rats treated with a silver sulfadiazine drug (SWISS PHARMACEUTICAL CO., LTD.). Each group contained three rats. The drugs were topically applied on the wounds at an amount of 0.35 g per cm$^2$ twice a day until hairs grew up.

Clinical Wound Evaluation:

The evaluation methods analogous to those in Example 3 were used and the sizes of the wounds were measured and given in Table 5.

TABLE 5

| | G1 | | G2 | | G3 | |
|---|---|---|---|---|---|---|
| Day | Wound area (mm$^2$) | Change of initial area (%) | Wound area (mm$^2$) | Change of initial area (%) | Wound area (mm$^2$) | Change of initial area (%) |
| 1 | 1260.00 | 100.00 | 1140.67 | 100.00 | 1776.33 | 100.00 |
| 5 | 938.67 | 74.50 | 1053.33 | 92.34 | 744.00 | 41.88 |
| 11 | 285.33 | 22.65 | 428.00 | 37.52 | 154.67 | 8.71 |
| 14 | 188.00 | 14.92 | 234.67 | 20.57 | 34.67 | 1.95 |
| 18 | 0.00 | 0.00 | 141.33 | 12.39 | 0.00 | 0.00 |
| 24 | 0.00 | 0.00 | 64.67 | 5.67 | 0.00 | 0.00 |
| 31 | 0.00 | 0.00 | 41.33 | 3.62 | 0.00 | 0.00 |
| 37 | 0.00 | 0.00 | 32.37 | 2.86 | 0.00 | 0.00 |

In the progress of the wound healing, the wounds treated with the ointment according to the invention were cured without scar and the skin color was as the same as the normal. However, scars were formed on the wounds treated with silver sulfadiazine drug. In addition, the wounds of the rats were cured on Day 18 faster than those with a conventional silver sulfadiazine drug that remained 2.86% of area of wound on Day 37.

New hair growth scores were also estimated and recorded. The new hair growth scores were defined as follows: "−2" referring to no new hair growth with some eschar and erythema; "−1" referring to no new hair growth with some erythema; "0" referring to no new hair growth with normal skin; "+1" referring to some new hair growth; and "+2" referring to new hair growth of approximately 50% of the wound area.

The new hair growth scores were listed in Table 6:

TABLE 6

| | Score | | |
|---|---|---|---|
| Day | G1 | G2 | G3 |
| 15 | −2 | −2 | 0 |
| 18 | −2 | −2 | 1 |
| 21 | −1 | −1 | 1 |
| 24 | −1 | −1 | 1 |
| 27 | −1 | −1 | 1 |
| 30 | −1 | −1 | 1 |
| 33 | −1 | −1 | 1 |
| 35 | −1 | −1 | 1 |

As shown in Table 6, the ointment according to the invention was more effective in new hair growth than the conventional silver sulfadiazine drug. New hair growth was observed when treating Pharmaceutical composition according to the invention on Day 18, and 50% of new hair growth was observed on Day 35. Neither erythema nor eschar was found in the wounds treated with Pharmaceutical composition according to the invention. However, not hair growth was observed when treating the conventional drug.

Histological Evaluation of Skin:

After the wounds were completely healed, the skin tissues of each rat were taken and anaesthetized for histological examination using the evaluation methods as described by B. Hafemann et al. (B. Hafemann et al. Use of a collagen/elastin-membrane for the tissue engineering of dermis. *Burns.* 1999;25:373–384.). The samples were taken and stored in formaldehyde. Each specimen was embedded in a paraffin block, and thin sections were prepared, and stained by using the hematoxylin-eosin method. The specimens were observed under an optical microscope, and a transmission electron microscope.

Figure 5:
FIG. 5 illustrates the result of histological examination of deep partial thickness burn wounds without treatment in Example 5.
Figure 6:
FIG. 6 illustrates the result of histological examination of deep partial thickness burn wounds treated with silver sulfadiazine drug in Example 5.
Figure 7:
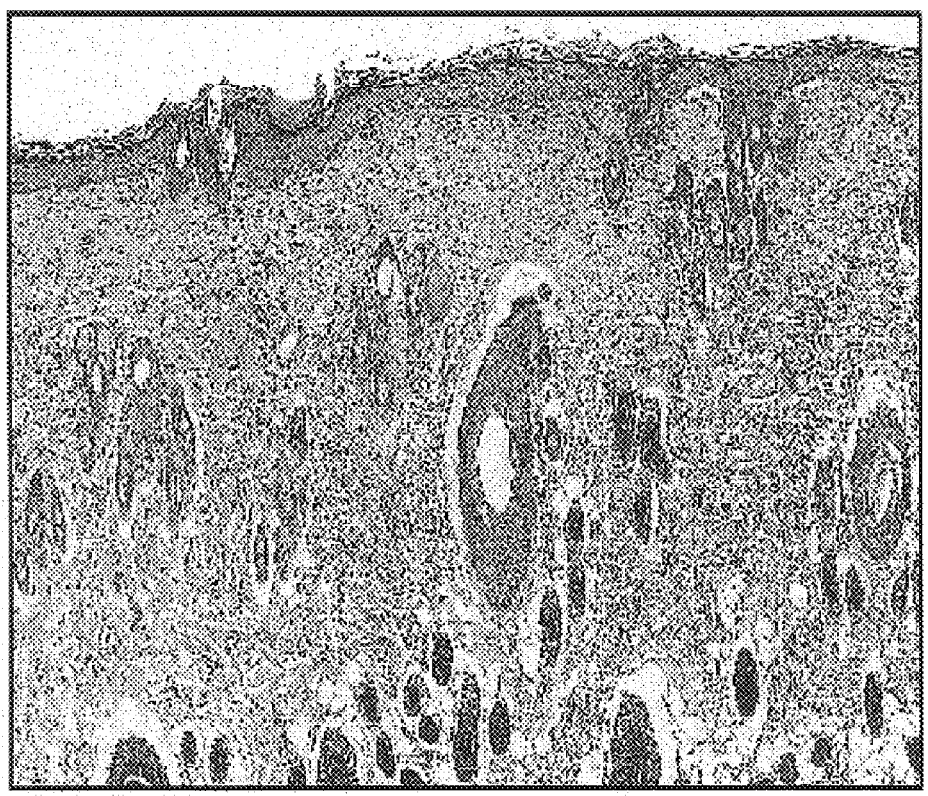
FIG. 7 illustrates the result of histological examination of deep partial thickness burn wounds treated with the ointment according to the invention in Example 5.

The results of the histological examination showed that the thickness of epithelium tissues of the rats without treatment (as shown in FIG. 5) was not even, and the granular layer was thickened. The fiber layer was observed in the deep dermal. In the group of rats treated with the conventional silver sulfadiazine drug (as shown in FIG. 6) were also shown to have uneven thickness of epithelium tissues. The fiber layer was observed in the deep dermal, and the fair follicles were destroyed. On the other hand, the wounds (as shown in FIG. 7) treated with the ointment according to the invention appeared to be normal, and a large number of hair follicles were regenerated. The fiber layer was observed in the surface area of dermal.

EXAMPLE 6

Effects on Large Area Full Thickness Skin Wounds in Rats

Treatment of Animals:

The male adult Sprague-Dawley rats were purchased from Laboratory Animal Center of the National Cheng Kung University in Taiwan. The rats weighting 300 to 350 g were anaesthetized with 25 to 40 mg/Kg of ketamine HCl. The back of each rat was thoroughly clipped using an electrical clipper. Each rat was caged alone and feed with chow and water. For each rat, the full thickness skin at an area of 4.0×4.0 $cm^2$ was excised, wherein the full thickness skin comprises epidermis, dermis, and panniculus camosus.

Dosage and Frequency:

The experiment group of rats was treated with the ointment comprising Fraction 9 as given in Example 5. One comparative group (G2) of rats treated with a silver sulfadiazine drug (SWISS PHARMACEUTICAL CO., LTD.) was also provided. Each group contained five rats. The ointments were topically applied on the wounds at an amount of 0.75 g per $cm^2$ and 0.1 to 0.2 cm height. All the wounds were dressed by sterile gauze and elastic bandage, and the dressing was changed everyday.

The evaluation methods analogous to those in Example 3 were used and the sizes of the wounds were measured and given in Table 7.

TABLE 7

| Day | silver sulfadiazine drug | | Ointment comprising Fraction 3 | |
|---|---|---|---|---|
| | Wound area ($mm^2$) | Change of initial area (%) | Wound area ($mm^2$) | Change of initial area (%) |
| 1 | 1977.60 | 100.00 | 1957.60 | 100.00 |
| 3 | 1763.20 | 89.16 | 1784.80 | 91.17 |
| 5 | 1444.80 | 73.06 | 1506.40 | 76.95 |
| 7 | 990.40 | 50.08 | 1265.60 | 64.65 |
| 9 | 556.00 | 28.11 | 768.80 | 39.27 |
| 11 | 429.60 | 21.72 | 456.80 | 23.33 |
| 13 | 368.80 | 18.65 | 385.60 | 19.70 |
| 15 | 283.20 | 14.32 | 299.20 | 15.28 |
| 17 | 208.80 | 10.56 | 236.80 | 12.10 |
| 19 | 166.00 | 8.39 | 238.40 | 12.18 |
| 21 | 131.00 | 6.62 | 161.60 | 8.26 |
| 23 | 119.00 | 6.02 | 123.20 | 6.29 |
| 25 | 87.00 | 4.40 | 88.00 | 4.50 |
| 27 | 45.00 | 2.28 | 76.00 | 3.88 |
| 29 | 40.00 | 2.02 | 56.00 | 2.86 |
| 31 | 35.00 | 1.77 | 34.40 | 1.76 |

TABLE 7-continued

| Day | silver sulfadiazine drug | | Ointment comprising Fraction 3 | |
|---|---|---|---|---|
| | Wound area ($mm^2$) | Change of initial area (%) | Wound area ($mm^2$) | Change of initial area (%) |
| 35 | 18.00 | 0.91 | 20.00 | 1.02 |
| 33 | 16.00 | 0.81 | 8.00 | 0.41 |
| 37 | 0.00 | 0.00 | 0.00 | 0.00 |

In the progress of the wound healing, the wounds treated with the ointment according to the invention were cured without allergy. However, scars were formed on the wounds treated with silver sulfadiazine drug. In addition, severe allergy was observed in the wounds treated with silver sulfadiazine drug. The healing rate of the rats treated with the pharmaceutical composition according to the invention (about 25 to 31 days) was faster than that with the silver sulfadiazine drug (about 37 days).

Histological Evaluation of Skin:

The method for histological evaluation was as described in Example 5.

The results of the histological examination taken on Day 45 showed that the wounds treated with the conventional silver sulfadiazine drug were observed to have the fiber layer in the deep dermal. Some epithelium cells died and form the callus. Chronic inflammation and eosinophils infiltration were both observed in the dermal. Some fiber also formed 0.5 cm away from the wound.

In the group of rats treated with the ointment according to the invention, the newborn epithelium was even, and a large amount of hair follicles were generated. Only little fiber formed.

Figure 8:
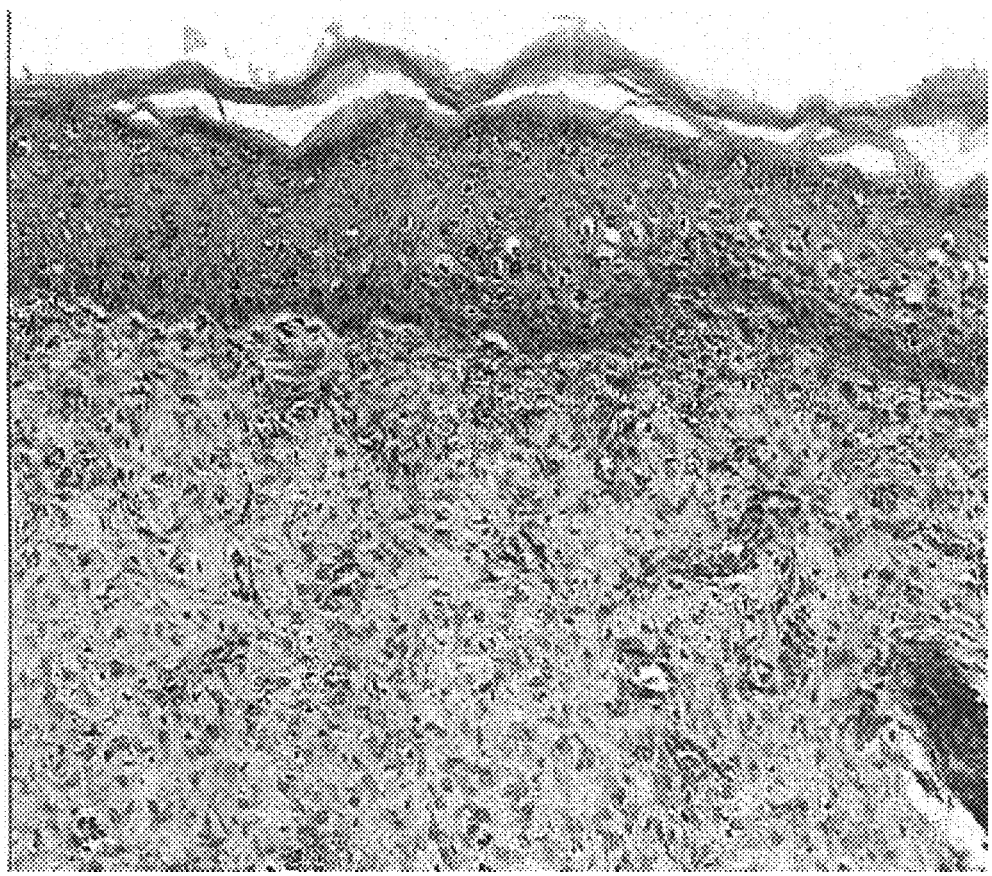
FIG. 8 illustrates the result of histological examination of large area full thickness skin wounds treated with silver sulfadiazine drug in Example 6.

The results of the histological examination taken on Day 95 showed that the wounds treated with the conventional silver sulfadiazine drug were observed to have the uneven epithelium layer (as shown in FIG. 8). Fiber layer was form in the deep dermal. A small amount of hair follicles was generated.

Figure 9:
FIG. 9 illustrates the result of histological examination of large area full thickness skin wounds treated with the ointment according to the invention in Example 6.

In the group of rats treated with the ointment according to the invention, the newborn epithelium was even, and a large amount of hair follicles were generated (as shown in FIG. 9).

EXAMPLE 7

Effects on Local Electron Irradiation Skin Injuries

Treatment of Animals:

The female adult Sprague-Dawley rats were purchased from Laboratory Animal Center of the National Cheng Kung University in Taiwan. The rats weighting 250 to 300 g were caged alone and feed with chow and water.

The irradiation of the rats were performed by using the methods analogous to that as described by John E. Moulder and James J. Fischer (RADIATION REACTION OF RAT SKIN: The role of the Number of Fractions and the Overall Treatment Time. *Cancer* June 1976;37(6):2762–2767). The rats were anaesthetized with 40 to 50 mg/Kg pentobarbital sodium salt (TCI.TOKYO) intraperitoneally before irradiation. Skin over the gluteus area was shaved completely and the area of the desired radiation of 2×2 $cm^2$ were marked on the right and left gluteus before irradiation. An electron beam of 6 MeV energy produced by a linear accelerator (Varian Associates, Inc., CA, U.S.A.) was applied for irradiation.

Fractional and single dosage irradiations were tested. In fractional irradiation, three rats were subject to irradiation on the right and left gluteus areas. The radiation was applied twice every week for 5 weeks, and the total dose was 37.5 Gy on each area.

Dosage and Frequency:

The irradiation injuries in the fractional irradiation were treated with the ointment comprising Fraction 9 (G1) as given in Example 5 after the irradiation once a day at the dosage of 0.25 g/cm², and the irradiation injuries in the single dosage irradiation were treated twice a day. The rats without treatment were used as a control (G2). One blank group (G3) of rats without receiving radiation was as a blank.

Clinical Evaluation:

The skin reaction scores (Yoshinao Abe and Muneyasu Urano, Fraction side-dependent Acute Skin Reaction of Mice after Multiple Twice-A-Day Doses. Int. *J. Radiation Oncology Biol. Phys.* 1990 February;18(2):359–364; Yu-Jen Chen et al. The Effect of Tetrandrine and Extracts of Centella asiatica on Acute Radiation Dermatitis in Rats. *Biol. Pharm. Bull.* 1999 July;22(7):703–706) had been evaluated and recorded for 30 days after irradiation. The skin reaction scores were defined as follows: "0" indicating normal skin; "0.5" indicating slight epilation occurring at less than 50% of the radiated area, or discoloration of hair; "1.0" indicating epilation occurring at about 50% of the radiated area; "1.5" indicating epilation occurring at more than 50% of the radiated area and some epilation with red skin; "2.0" indicating complete epilation and dry desquamation occurring at less than 50% of the radiated area; "2.5" indicating dry desquamation occurring at more than 50% of the radiated area; "0.0" indicating some moist desquamation occurring; "3.5" indicating moist desquamation at most of the area.

The skin reaction scores were evaluated and given in Table 8.

TABLE 8

| Day | skin reaction scores | | |
|---|---|---|---|
|  | G1 | G2 | G3 |
| 0 | 0.00 | 0.00 | 0.00 |
| 3 | 0.00 | 0.50 | 0.00 |
| 6 | 0.00 | 0.50 | 0.00 |
| 9 | 0.00 | 0.83 | 0.00 |
| 12 | 0.00 | 0.83 | 0.00 |
| 15 | 0.00 | 0.83 | 0.00 |
| 18 | 0.00 | 0.83 | 0.00 |
| 21 | 0.10 | 0.83 | 0.00 |
| 24 | 0.00 | 0.83 | 0.00 |
| 29 | 0.00 | 1.00 | 0.00 |

In G1, tear early and little hair damage were found in the wounds, and the skin showed no allergy.

The results were similar to those of the fractional irradiation test.

Histological Evaluation of Skin:

The evaluation methods analogous to those in Example 5 were used.

Figure 10:
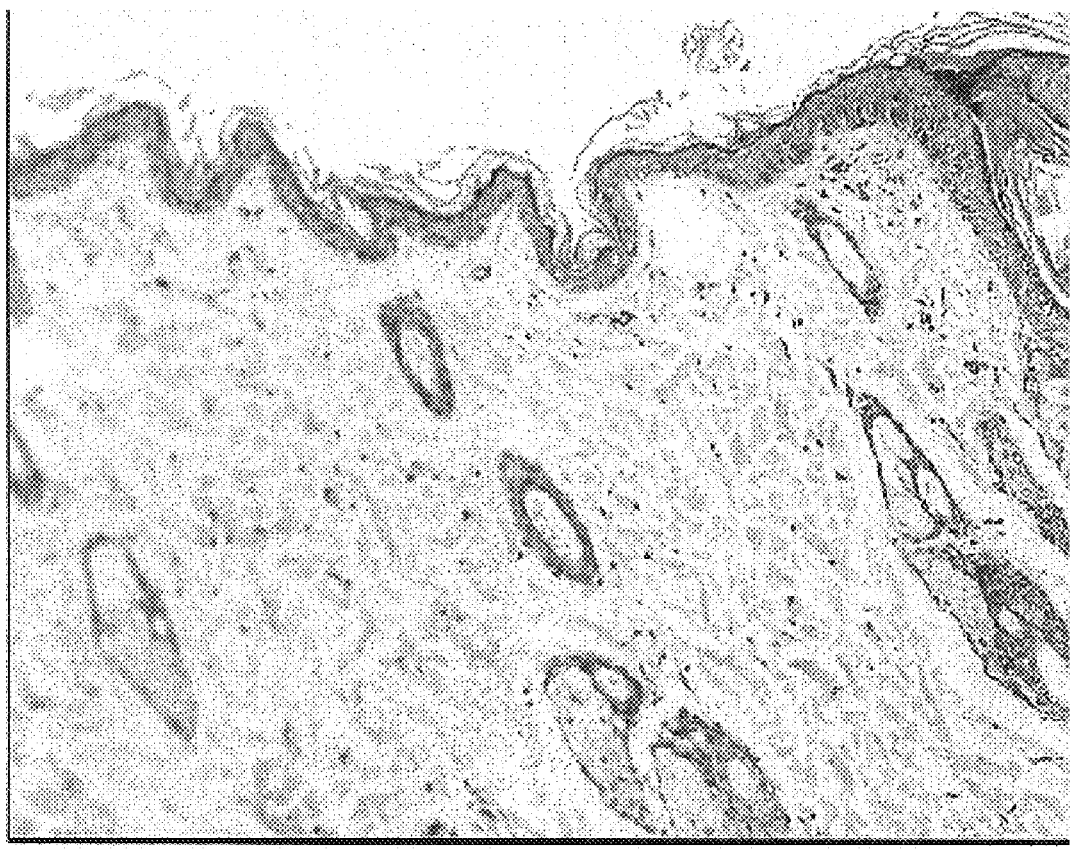
FIG. 10 illustrates the result of histological examination of irradiation skin injury treated with the ointment according to the invention in Example 7.

In G1 (as shown in FIG. 10), the epidermal cells were found to cover multi-layered epithelium cells. A large amount of hair follicles were also regenerated.

Figure 11:
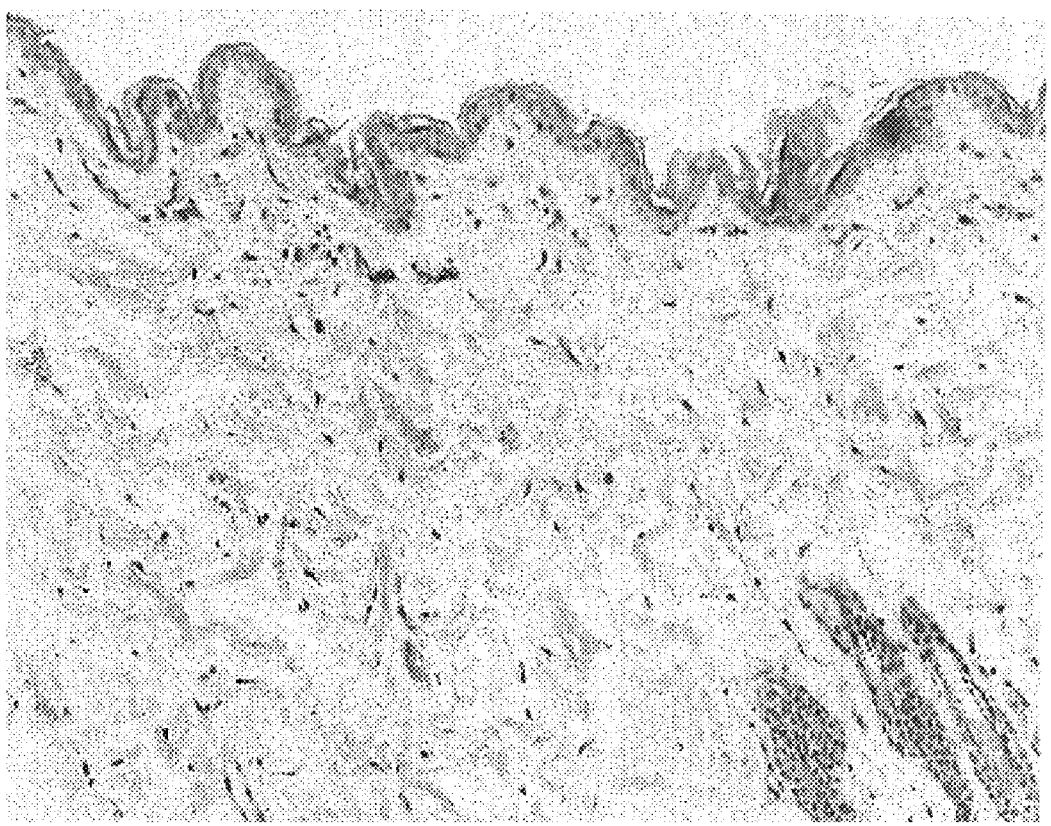
FIG. 11 illustrates the result of histological examination of irradiation skin injury without treatment in Example 7.

In G2 (as shown in FIG. 11), only small amount of hair follicles were observed.

Figure 12:
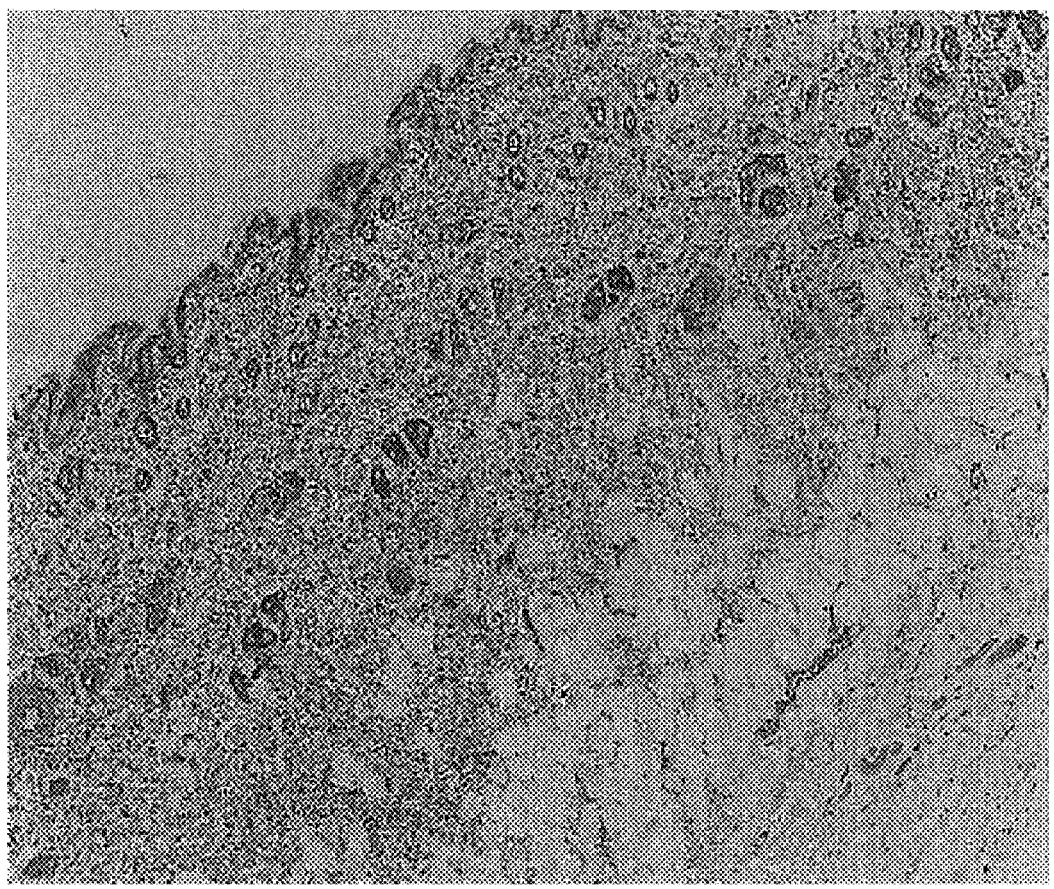
FIG. 12 illustrates the result of normal tissue in Example 7.

In G3 (as shown in FIG. 12), the tissues were taken as control.

The tissues of the wounds with treatment were dense but those without treatment were loosing.

EXAMPLE 8

Effects on Dermatitis on Rabbit Ears

Figure 13:
FIG. 13 illustrates the picture of dermatitis on rabbit ear before treatment in Example 8.

Dermatitis on rabbit ear was found to have symptoms of redness, swell, inflammation, ulcer and bleeding as shown in FIG. 13.

The wounds were applied with the ointment according to the invention that comprises Fraction 10 similar to Fraction 3 except the content of alcohol being 0% as given in Example 2 for 3 days.

Figure 14:
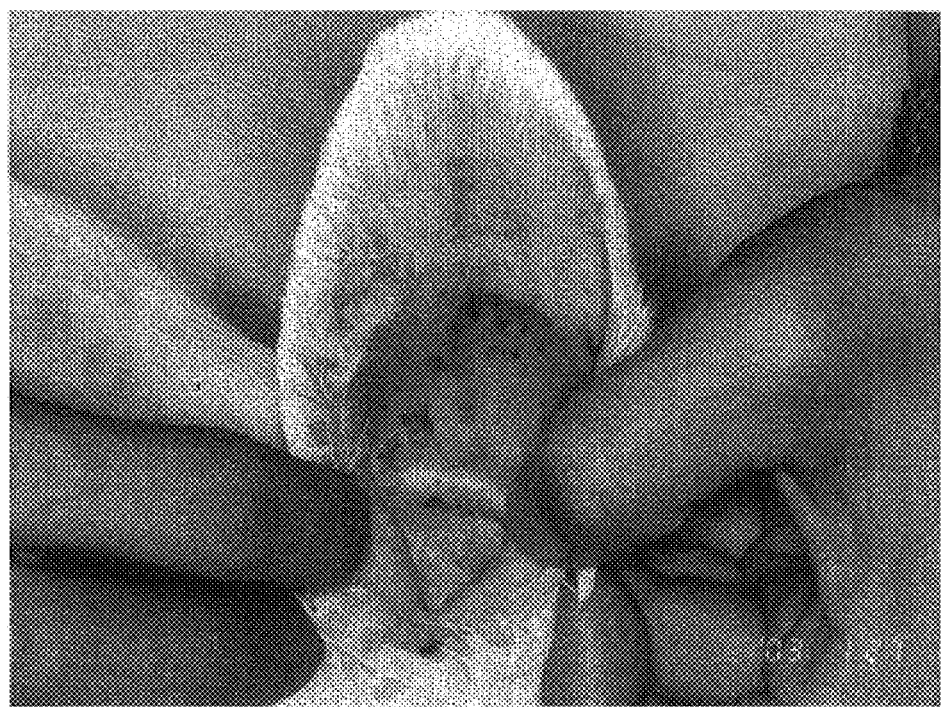
FIG. 14 illustrates the picture of dermatitis on rabbit ear after treated with the ointment according to the invention on Day 1 in Example 8.

On Day 1, the ulcer disappeared and the redness was alleviated. The hair follicles appeared as shown in FIG. 14.

Figure 15:
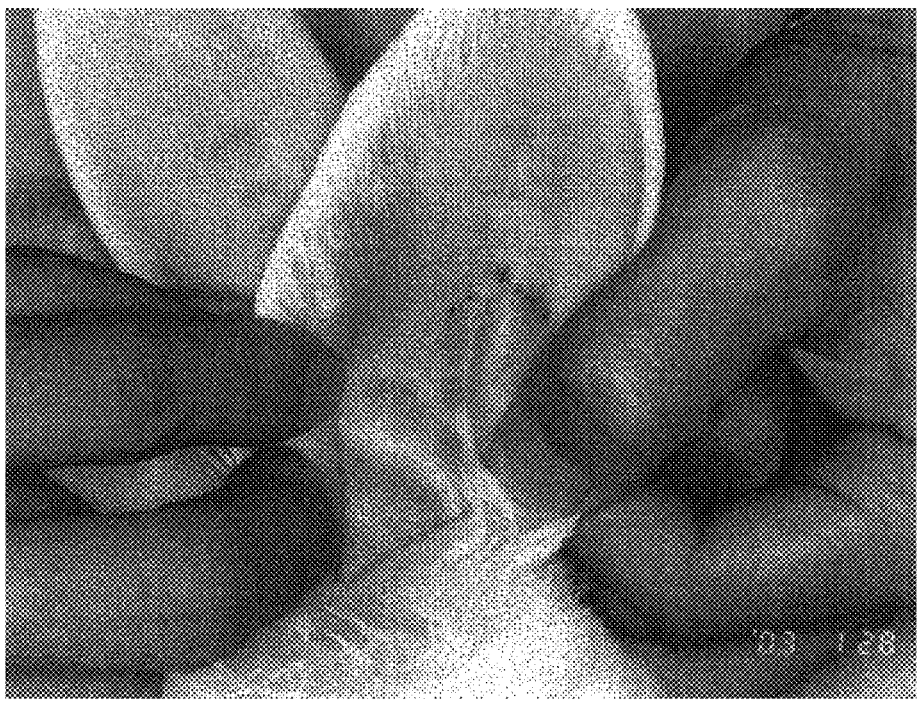
FIG. 15 illustrates the picture of dermatitis on rabbit ear after treated with the ointment according to the invention on Day 2 in Example 8.

On Day 2, the skin tissue was recovered and only slightly redness was observed. The hair follicles were obviously as shown in FIG. 15.

Figure 16:
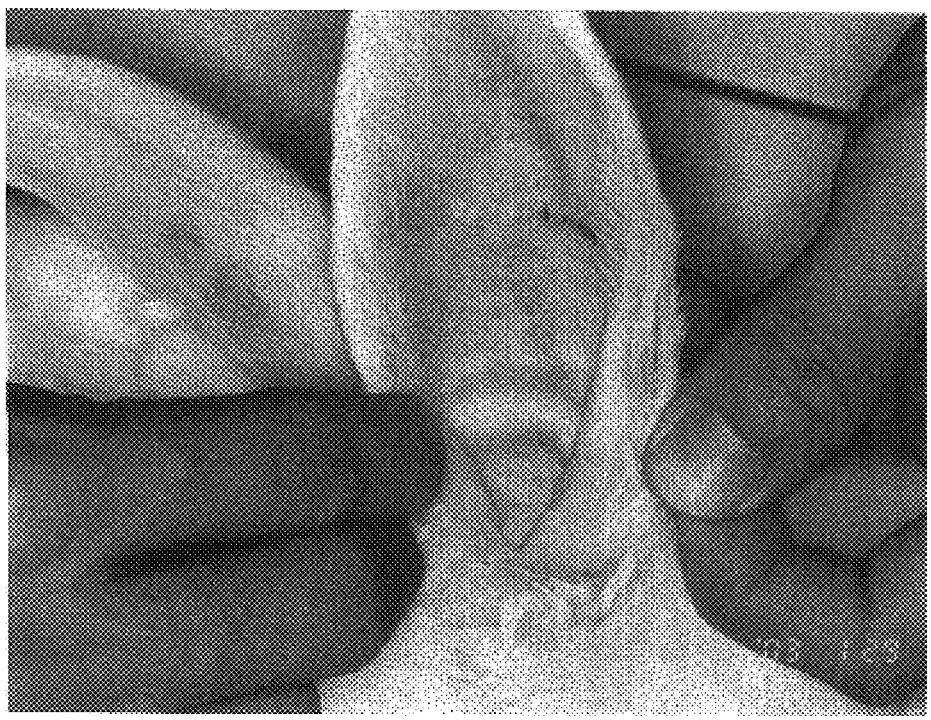
FIG. 16 illustrates the picture of dermatitis on rabbit ear after treated with the ointment according to the invention on Day 3 in Example 8.

On Day 3, the skin tissue and color were normal. The hair grew on the hair follicles as shown in FIG. 16.

EXAMPLE 9

Effects on Diabetes Mellitus Wounds

Figure 17:
FIG. 17 illustrates the picture of diabetes mellitus wounds in Example 9.
Figure 18:
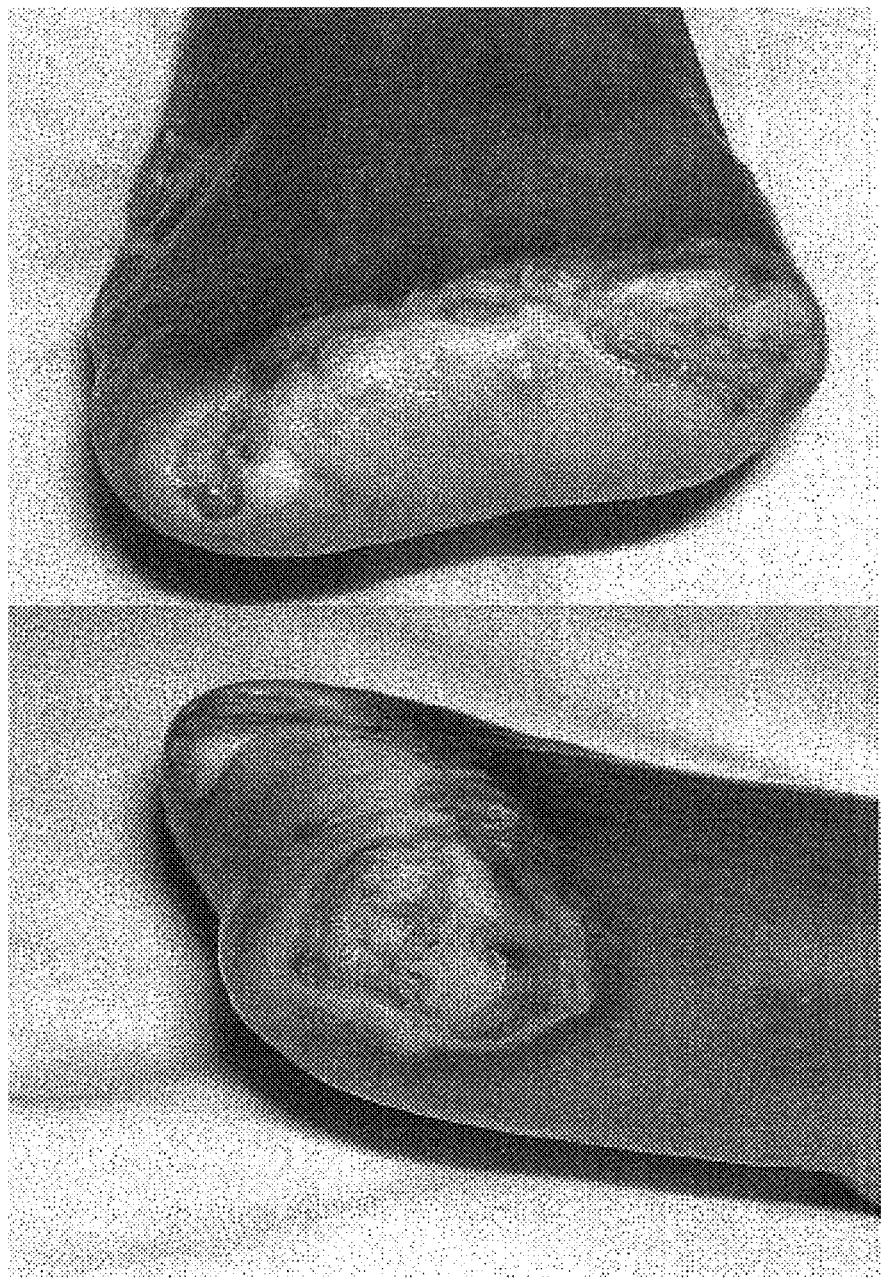
FIG. 18 illustrates the picture of diabetes mellitus wounds in Example 9.

A 68-year-old male had been suffered with diabetes mellitus for 20 years. His toes of left foot were performed with amputation. The wounds showed severe gangrene change as shown in FIG. 17. All toes on his right foot were amputated but the wound healing was not good as shown in FIG. 18.

The ointment comprising Fraction 9 was applied on the wounds 2 to 3 times a day.

Figure 19:
FIG. 19 illustrates the picture of diabetes mellitus wounds treated with the ointment according to the invention for 2 months in Example 9.

After the treatment of the left foot for 2 months (as shown in FIG. 19), some granulation tissues were noted, and the wound was started to healing without more necrosis.

Figure 20:
FIG. 20 illustrates the picture of diabetes mellitus wounds treated with the ointment according to the invention for 5 months in Example 9.
Figure 21:
FIG. 21 illustrates the picture of diabetes mellitus wounds treated with the ointment according to the invention for 5 months in Example 9.

After the treatment of the left foot for 5 months (as shown in FIG. 20), the wound was completely healed without scar. The right foot (as shown in FIG. 21) was also completely healed without scar.

EXAMPLE 10

Effects on Chronic Stasis Ulcer

Figure 22:
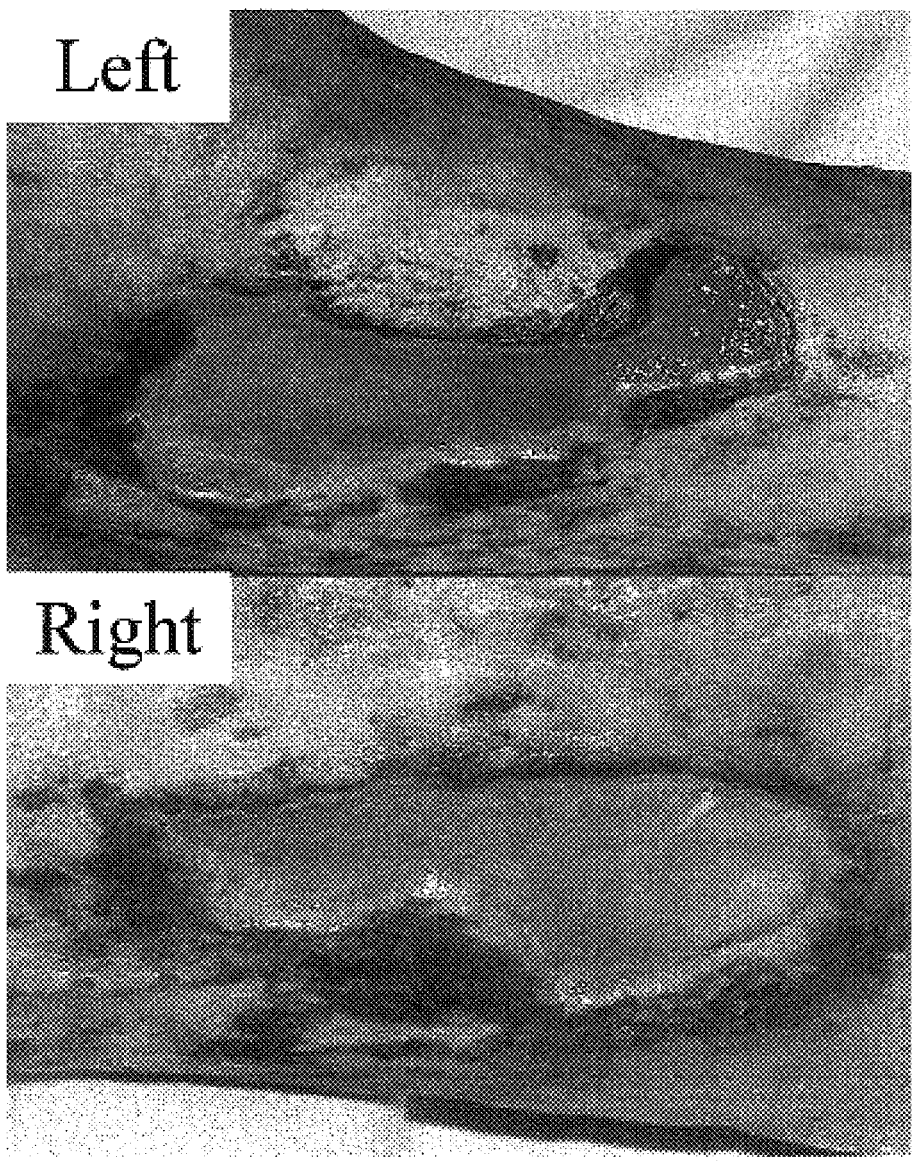
FIG. 22 illustrates the picture of chronic stasis ulcer in Example 10.

Bilateral lower legs of an 80-year-old male had been suffered with hyperpigmentation and stasis ulcer for 20 years as shown in FIG. 22.

The ointment comprising Fraction 9 was applied on the wounds 2 to 3 times a day.

Figure 23:
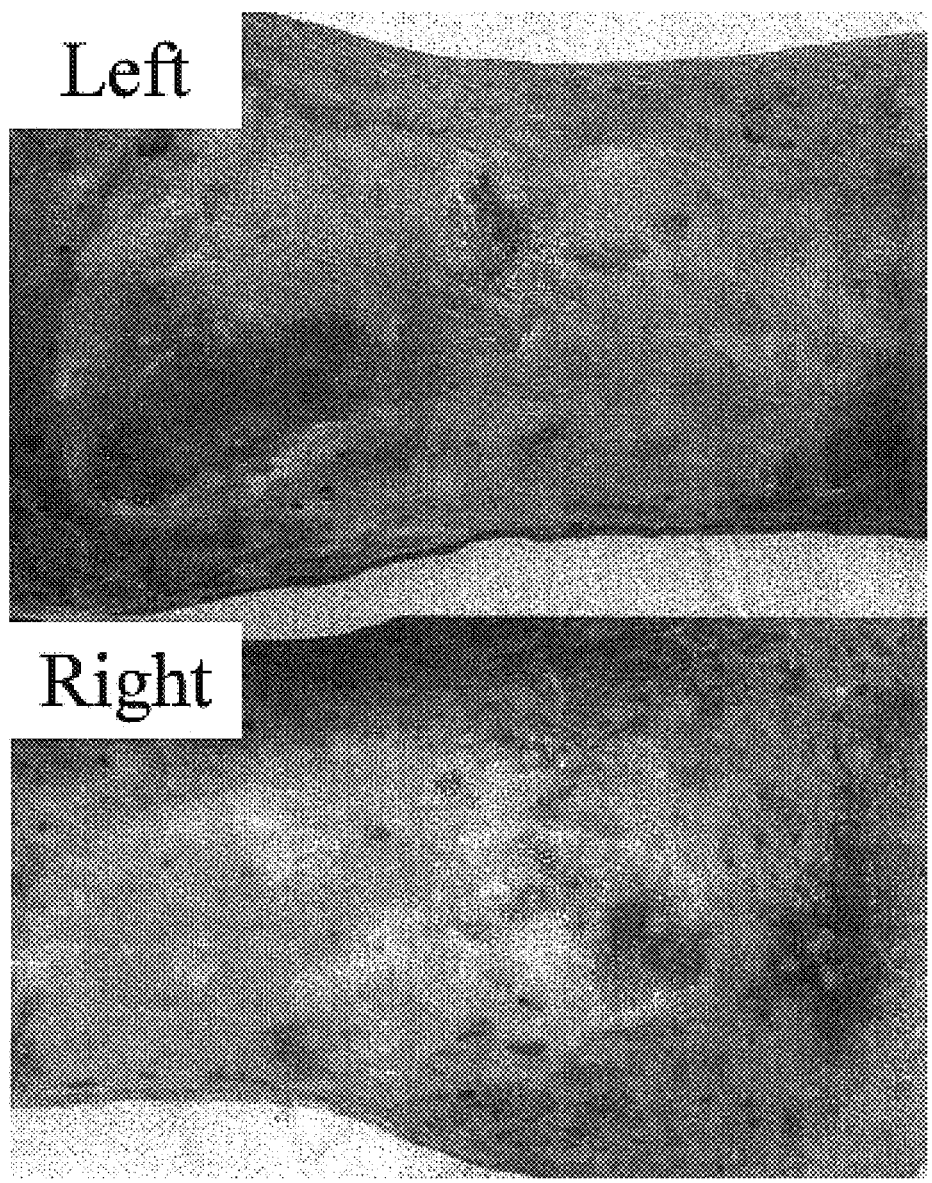
FIG. 23 illustrates the picture of chronic stasis ulcer treated with the ointment according to the invention for 2 weeks in Example 10.

After the treatment of the feet for 2 weeks (as shown in FIG. 23), the wound was started to healing.

Figure 24:
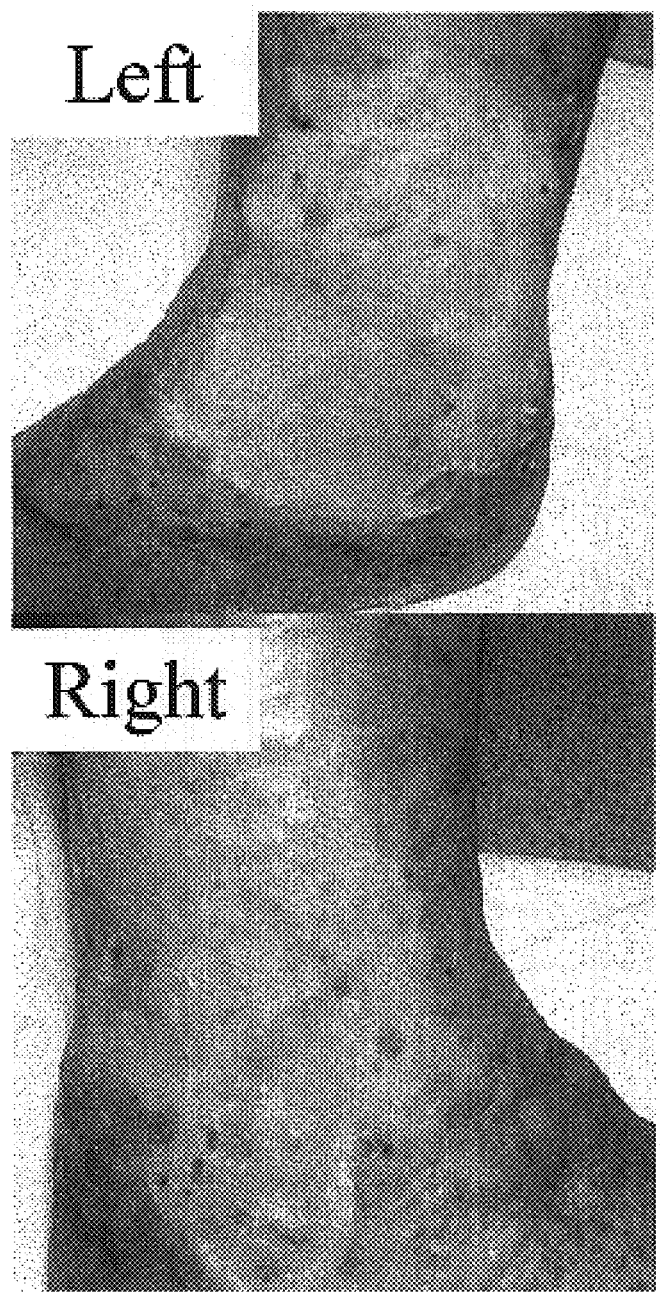
FIG. 24 illustrates the picture of chronic stasis ulcer treated with the ointment according to the invention for 4 weeks in Example 10.

After the treatment of the feet for 4 weeks (as shown in FIG. 24), the wound was completely healed without scar.

EXAMPLE 11

Effects on Ecchymosis

Figure 25:
FIG. 25 illustrates the picture of ecchymosis in Example 11.

A female patient had ecchymosis caused by an accident (as shown in FIG. 25).

The wounds were pretreated with a cold compress once a day for three days, and then applied with the ointment comprising Fraction 9 2 to 3 times a day.

Figure 26:
FIG. 26 illustrates the picture of ecchymosis treated with the ointment according to the invention for 3 days in Example 11.
Figure 27:
FIG. 27 illustrates the picture of ecchymosis treated with the ointment according to the invention for 7 days in Example 11.

The ecchymosis disappeared and the wounds were healed on the third day post treatment as shown in FIG. 26. The color of the scar that was already present before the car accident was also flattened and lightened after treating for 7 days (as shown in FIG. 27).

EXAMPLE 12

Effects on Abrasion

Figure 28:
FIG. 28 illustrates the picture of abrasion wounds in Example 12.

A female patient had skin abrasion caused by an accident as shown in FIG. 28.

The ointment comprising Fraction 9 was applied on the wounds 2 to 3 times a day.

Figure 29:
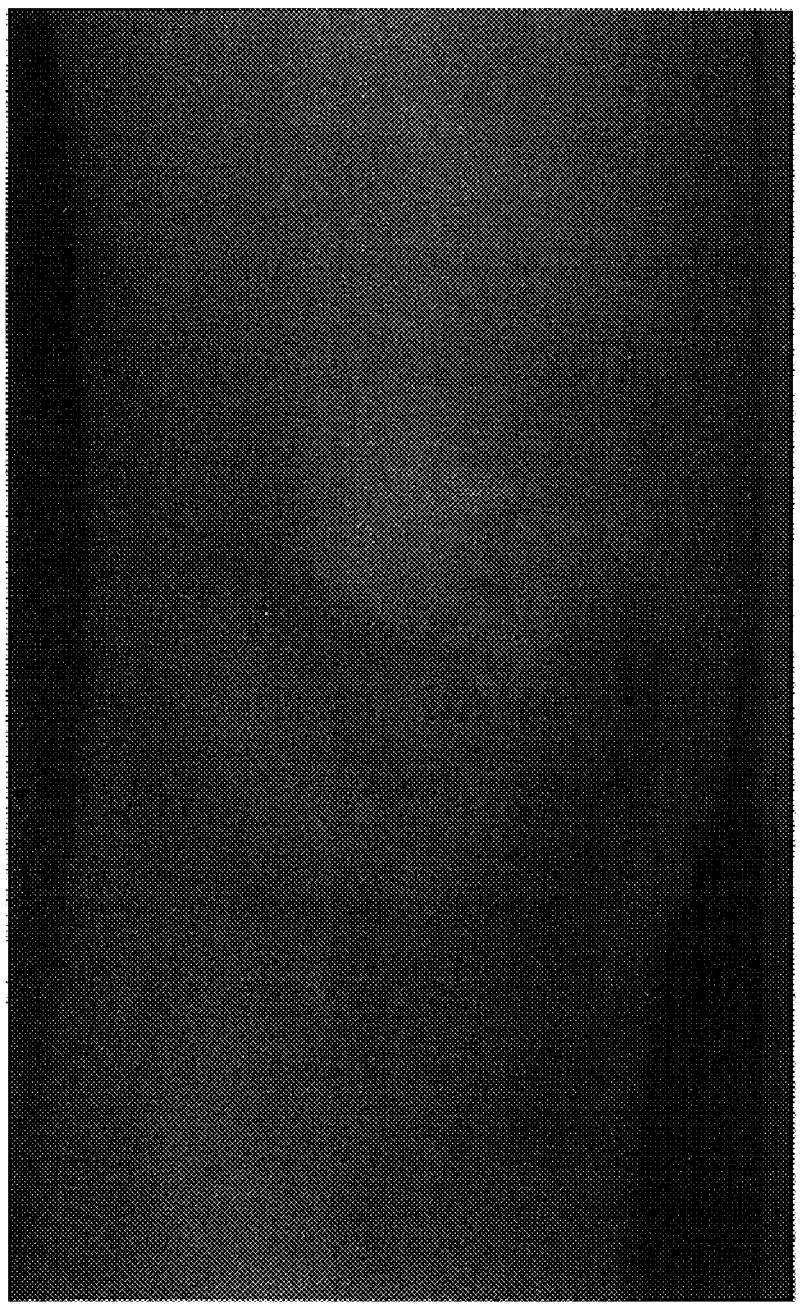
FIG. 29 illustrates the picture of ecchymosis treated with the ointment according to the invention for 7 days in Example 12.

The wounds were healed after the treatment for 7 days (as shown in FIG. 29).

EXAMPLE 13

Effects on Suture Wounds

A male patient had serious laceration wounds on the philtrum with 3 cm break and 20-stitches suture, nose beam with 0.8 cm and 4-stitches suture and upper lip with 1 cm break and 6-stitches suture and 1.5 cm break and 8-stitches suture.

The ointment comprising Fraction 9 was applied on the wounds 2 to 3 times a day.

Figure 30:
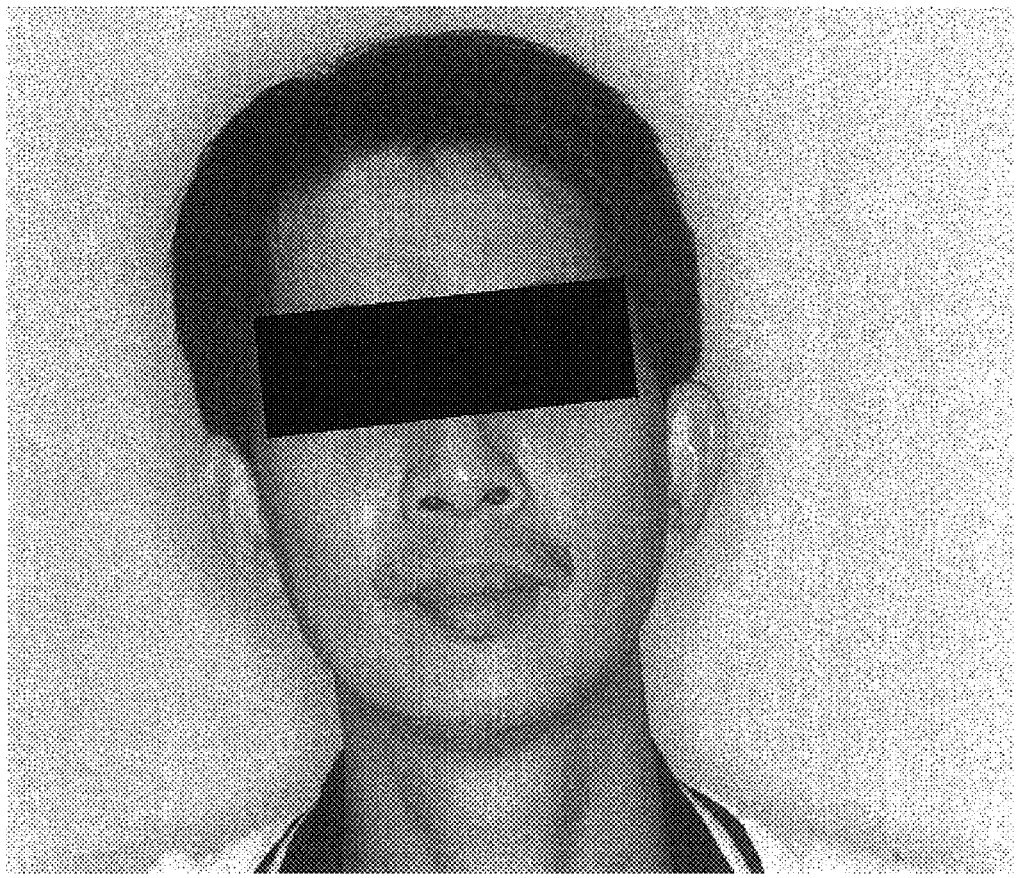
FIG. 30 illustrates the picture of suture wounds treated with the ointment according to the invention in Example 13.

The wounds were healed completely without scar (as shown in FIG. 30).

EXAMPLE 14

Effects on Atopic Dermatitis

Figure 31:
FIG. 31 illustrates the picture of atopic dermatitis in Example 14.

A 4.5-year-old female had chronic atopic dermatitis. The skin of the neck and upper thorax was itchy, redness, swelling, crackling, weeping, crusting and scaling after long-term topical corticosteroid therapy as shown in FIG. 31.

The ointment comprising Fraction 10 was applied on the wounds 2 to 3 times a day.

Figure 32:
FIG. 32 illustrates the picture of atopic dermatitis treated with the ointment according to the invention for 1 week in Example 14.

After the treatment for 1 week (as shown in FIG. 32), the itching, redness, swelling, cracking, weeping, crusting, and scaling were reduced and decreased.

Figure 33:
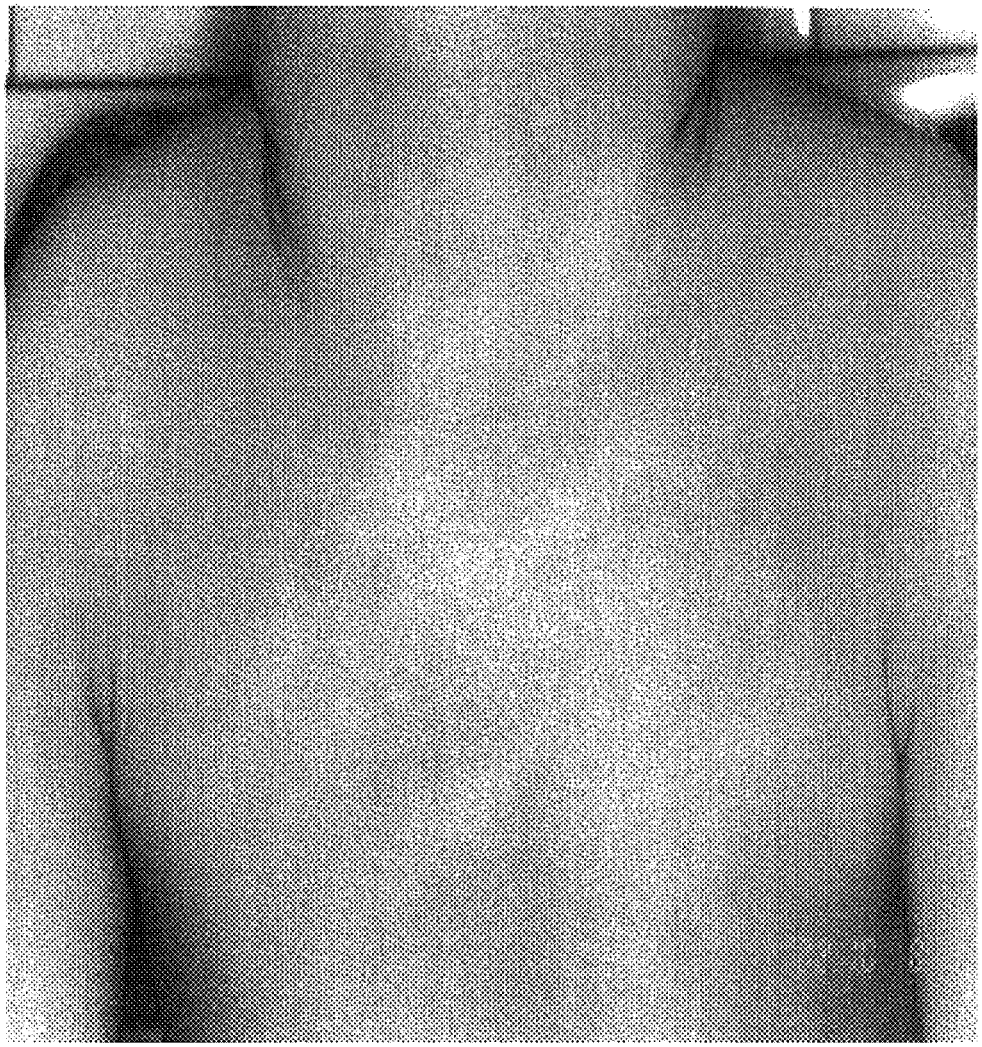
FIG. 33 illustrates the picture of atopic dermatitis treated with the ointment according to the invention for 4 weeks in Example 14.

After the treatment for 4 weeks (as shown in FIG. 33), the skin lesions were almost subsided.

Figure 34:
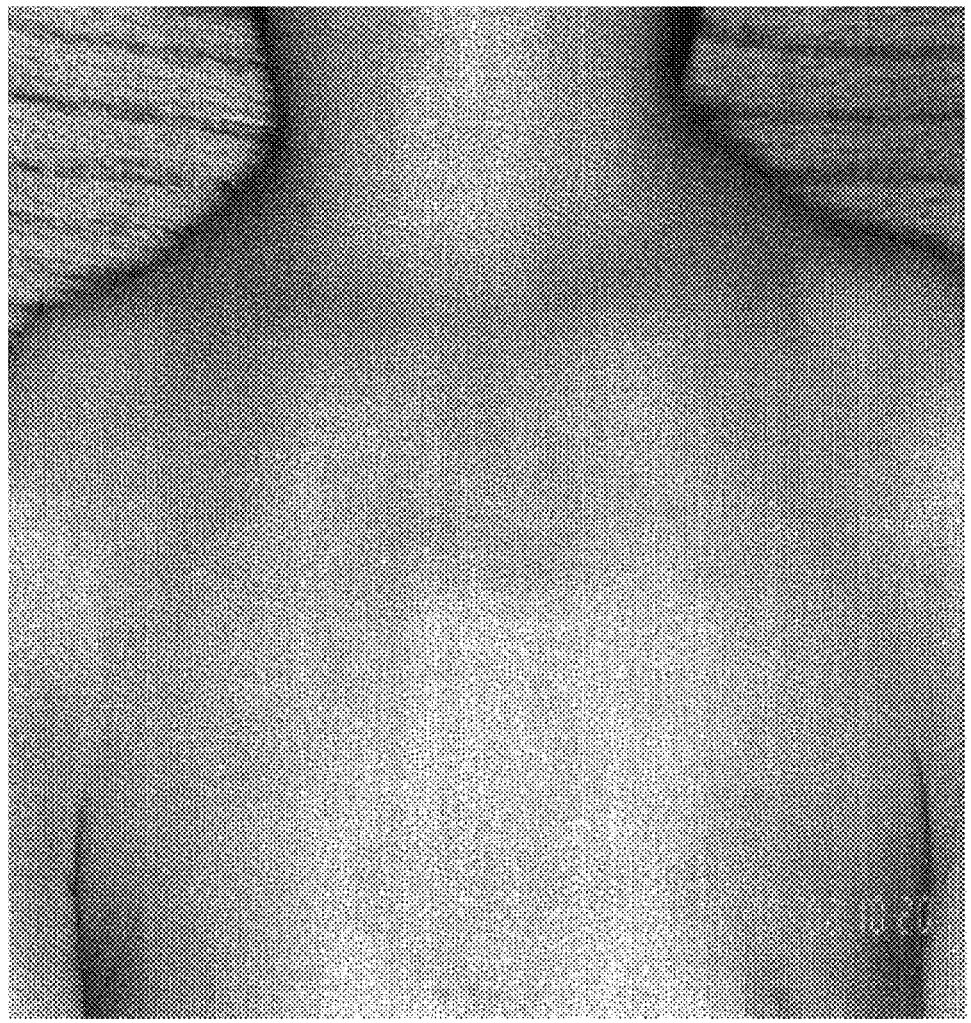
FIG. 34 illustrates the picture of atopic dermatitis treated with the ointment according to the invention for 6 weeks in Example 14.

After the treatment for 6 weeks (as shown in FIG. 34), the skin lesions were completely healed with no rebound effect later.

While embodiments of the present invention have been illustrated and described, various modifications and improvements can be made by persons skilled in the art. The embodiments of the present invention are therefore described in an illustrative but not restrictive sense. It is intended that the present invention is not limited to the particular forms as illustrated, and that all the modifications not departing from the spirit and scope of the present invention are within the scope as defined in the appended claims.

What is claimed is:

1. A vapor fraction from seeds of *Glycine max* (L.) Merr., which vapor fraction is prepared by the process comprising the steps of:

(a) providing a crude extract of the seeds in an alcohol solution containing alcohol at the concentration lower than about 15% wt. or in water; and (b) vaporizing the crude extract at a barometric pressure lower than about 1 atm and at a temperature lower than about 110° C. to obtain the vapor fraction;

wherein a spectrogram of the 50 mL of the vapor fraction taken at 200 nm through a high performance liquid chromatography (HPLC) using Waters Sphersorb™-ODS2 column with an inner diameter (I.D.) of 4.6 mm, a length (L) of 250mm and a particle size of 5 mm comprises peaks at a retention time of 2.910, 5.190, 13.190, and 50.815 minutes with the coefficient of variation of 8%, where mobile phase is at 0 to 5 minutes is 95% $H_2O$/5% $CH_3CN$; at 5 to 30 minutes is 95% $H_2O$/5% $CH_3CN$ in gradient, at 30 to 80 minutes is 75% $H_2O$/25% $CH_3CN$ in gradient; at 80 to 100 minutes is 0% $H_2O$/100% $CH_3CN$ in gradient; at 100 to 101 minutes is 0% $H_2O$/100% $CH_3CN$ in gradient; and at 101 minute is 95% $H_2O$/5% $CH_3CN$ and a flow rate is 1 mL/min.

2. The vapor fraction according to claim 1, wherein the vapor fraction is collected in a liquid form by chilling the vapor.

3. The vapor fraction according to claim 1, wherein the concentration of alcohol is lower than about 5% wt.

4. The vapor fraction according to claim 1, wherein the crude extract in the step (a) is in water.

5. The vapor fraction according to claim 1, wherein the temperature in the step (b) ranges from about 60° C to about 110° C.

6. The vapor fraction according to claim 1, which has effects of treating skin injuries, treating dermatological disorders, stimulating cell regeneration, and stimulating hair growth.

7. A composition for treating skin injuries or dermatological disorders comprising an effective amount of the vapor fraction according to claim 1.

8. A composition according to claim 7 in the form of a pharmaceutical composition, a cosmetic composition or a skin cleaning composition.

9. The composition according to claim 7 further comprising an antimicrobial agent.

10. The composition according to claim 7 further comprising borneol, stearic acid, stearyl alcohol, palmitic acid, cetyl alcohol, beewax and polyoxy ethylene sorbitan monostearate.

11. A method for treating a skin injury or dermatological disorder in a patient comprising applying to the skin injury or dermatological disorder of said patient, the composition according to claim 7 in an amount effective for treating the skin injury, treating the dermatological disorder, stimulating cell regeneration, or stimulating hair growth.

12. The method according to claim 11, wherein the skin injuries or dermatological disorders are selected from the group consisting of burn injury, sunburns, irradiation injury, acute and chronic trauma, ecchymosis, dermatitis, macule, papule, nodule, vesicle, bulla, pustule, wheal, plaque, cyst, scales, crust, fissure, ulcer, acne, xeroderma, desquamation, itch, allergic dermatitis, exanthema, gangrene, chronic stasis ulcer, abrasion, atopic dermatitis, suture wounds, diabetes mellitus wounds, and hair follicle defect.

13. The method according to claim 11, wherein the skin injuries or dermatological disorders are selected from the group consisting of burn injury, irradiation injury, acute and chronic trauma, dermatitis, gangrene, chronic stasis ulcer, abrasion, atopic dermatitis, suture wounds, diabetes mellitus wounds, and hair follicle defect.

* * * * *